(12) United States Patent
Kogan

(10) Patent No.: US 8,168,639 B2
(45) Date of Patent: May 1, 2012

(54) HETEROTRICYCLIC COMPOUNDS AS SEROTONERGIC AND/OR DOPAMINERGIC AGENTS AND USES THEREOF

(75) Inventor: Vladimir Kogan, Rechovot (IL)

(73) Assignee: ATIR Holding S.A., Luxembourg (LU)

( * ) Notice: Subject to any disclaimer, the term of this patent is extended or adjusted under 35 U.S.C. 154(b) by 0 days.

(21) Appl. No.: 12/532,869

(22) PCT Filed: Sep. 24, 2007

(86) PCT No.: PCT/IL2007/001174
§ 371 (c)(1),
(2), (4) Date: Sep. 24, 2009

(87) PCT Pub. No.: WO2008/117269
PCT Pub. Date: Oct. 2, 2008

(65) Prior Publication Data
US 2010/0216807 A1    Aug. 26, 2010

Related U.S. Application Data

(63) Continuation-in-part of application No. PCT/IL2007/000404, filed on Mar. 28, 2007.

(60) Provisional application No. 60/879,531, filed on Jan. 10, 2007, provisional application No. 60/786,379, filed on Mar. 28, 2006.

(30) Foreign Application Priority Data

Mar. 28, 2007  (WO) .................. PCT/IL2007/000404

(51) Int. Cl.
*A61K 31/497* (2006.01)
*A61K 31/505* (2006.01)
*C07D 401/00* (2006.01)
*C07D 239/00* (2006.01)
*A01N 43/54* (2006.01)

(52) U.S. Cl. ................... 514/253.03; 514/267; 544/249; 544/361

(58) Field of Classification Search ............. 514/253.03, 514/267; 544/249, 361
See application file for complete search history.

(56) References Cited

U.S. PATENT DOCUMENTS
3,322,756 A    5/1967   Ruschig et al.
(Continued)

FOREIGN PATENT DOCUMENTS
EP              0465254      1/1992
(Continued)

OTHER PUBLICATIONS

Mehta, Pratibha, Synthesis of Substituted Pyrido[3,4-b]indole-3-carboxamides and Related Compounds as Benzodiazepine Receptor Agonists/antagonists, Indian journal of chemistry. Sect. B. Organic Chemistry, including Medicinal Chemistry, vol. 27B, Issue 2, 140 (1988).*

(Continued)

Primary Examiner — Andrew D Kosar
Assistant Examiner — Erich A Leeser

(57) ABSTRACT

Novel heterocyclic compounds of formula I:

A-B-D           Formula I or a pharmaceutically acceptable salt thereof,
wherein:
A is selected from the group consisting of a moiety having general Formula II and a moiety having general Formula III:

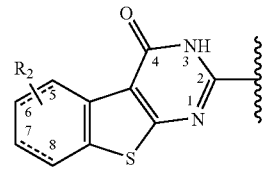

Formula II

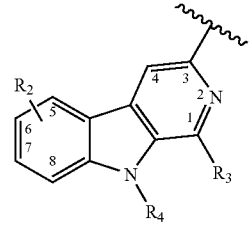

Formula III

B is a moiety selected from the group consisting of:

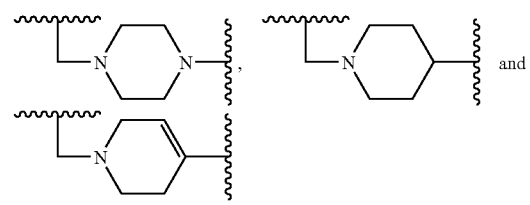

and

D is a moiety selected from the group consisting of:

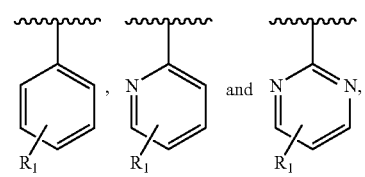

which exhibit a dopamine receptor (preferably a D4 receptor) and/or a serotonine receptor (preferably $5HT_{A1}$ agonistic activity), processes of preparing same, pharmaceutical compositions containing same and uses thereof in the treatment of medical conditions associated with the dopaminergic and/or serotonergic systems (e.g., sexual disorders, dyskinesia, anxiety) are disclosed.

52 Claims, 2 Drawing Sheets

U.S. PATENT DOCUMENTS

| | | | |
|---|---|---|---|
| 3,984,555 | A | 10/1976 | Amschler et al. |
| 4,835,157 | A | 5/1989 | Press et al. |
| 5,945,117 | A | 8/1999 | El-Rashidy et al. |
| 7,151,103 | B2 | 12/2006 | Borsini et al. |
| 2003/0087916 | A1 | 5/2003 | Lavielle et al. |
| 2004/0048853 | A1 | 3/2004 | Bergnes |
| 2004/0077667 | A1 | 4/2004 | Matsuoka et al. |
| 2010/0029671 | A1 | 2/2010 | Tworowski et al. |

FOREIGN PATENT DOCUMENTS

| | | | |
|---|---|---|---|
| EP | 1 724 267 | * | 11/2006 |
| EP | 1724267 | | 11/2006 |
| WO | WO 94/07869 | | 4/1994 |
| WO | WO 96/16657 | | 6/1996 |
| WO | WO 98/56792 | | 12/1998 |
| WO | WO 00/32590 | | 6/2000 |
| WO | WO 00/50417 | | 8/2000 |
| WO | WO 02/48117 | | 6/2002 |
| WO | WO 2004/018058 | | 3/2004 |
| WO | WO 2004/089312 | | 10/2004 |
| WO | WO 2007/110868 | | 10/2004 |
| WO | WO 2004/105700 | | 12/2004 |
| WO | WO 2005/005397 | | 1/2005 |
| WO | WO 2005/082887 | | 9/2005 |
| WO | WO 2007/011623 | | 1/2007 |
| WO | WO 2008/117269 | | 10/2008 |

OTHER PUBLICATIONS

International Preliminary Report on Patentability Dated Feb. 16, 2009 From the International Preliminary Examining Authority Re.: Application No. PCT/IL2007/001174.
Communication Pursuant to Article 94(3) EPC Dated Aug. 27, 2009 From the European Patent Office Re.: Application No. 07736144.2.
Communication Relating to the Results of the Partial International Search Dated Aug. 7, 2007 From the International Searching Authority Re.: Application No. PCT/IL2007/000404.
Communication Relating to the Results of the Partial International Search Dated Mar. 19, 2008 From the International Searching Authority Re: Application No. PCT/IL2007/001174.
International Preliminary Report on Patentability Dated Jul. 29, 2008 From the International Preliminary Examining Authority Re.: Application No. PCT/IL2007/000404.
International Search Report Dated Feb. 21, 2008 From the International Searching Authority Re.: Application No. PCT/IL2007/000404.
International Search Report Dated Oct. 29, 2008 From the International Searching Authority Re.: Application No. PCT/IL2007/001174.
Written Opinion Dated Feb. 21, 2008 From the International Searching Authority Re.: Application No. PCT/IL2007/000404.
Written Opinion Dated Oct. 29, 2008 From the International Searching Authority Re.: Appliation No. PCT/IL2007/001174.
Ambinter "Ambinter Stock Screening Collection", Database CHEMCATS, Chemical Abstracts Service, XP-002468185, Order No. From T5926242/ON-T0518-5380/ON, Oct. 2007.
Aurora "Aurora Screening Library", Aurora Fine Chemicals, Database CHEMCATS, Chemical Abstracts Service, Order No. Kenc-0060448, XP-002468184, Sep. 2007.
Official Action Dated Mar. 18, 2010 From the US Patent and Trademark Office Re.: U.S. Appl. No. 11/922,913.
Response Dated Dec. 24, 2009 to Communication Pursuant to Article 94(3) EPC of Aug. 27, 2009 From the European Patent Office Re.: Application No. 07736144.2.
Communication Pursuant to Article 94(3) EPC Dated Feb. 22, 2010 From the European Patent Office Re.: Application No. 07736144.2.
Response Dated Jun. 22, 2010 to Communication Pursuant to Article 94(3) EPC of Feb. 22, 2010 From the European Patent Office Re.: Application No. 07736144.2.
Response Dated Aug. 18, 2010 to Official Action of Mar. 18, 2010 From the US Patent and Trademark Office Re.: U.S. Appl. No. 11/922,913.
European Search Report and the European Search Opinion Dated Aug. 20, 2010 From the European Patent Office Re. Application No. 10153226.5.
Gupta et al. "Drugs Acting on the Central Nervous System. Syntheses of Substituted Quinazolones and Quinazolines and Triazepino- and Triazocinoquinazolinones", Journal of Medicinal Chemistry, XP002588388, 11(2): 392-395, 1968. P.392: Pharmacology, Ex.26.
Official Action Dated Sep. 29, 2010 From the US Patent and Trademark Office Re.: U.S. Appl. No. 11/922,913.
Communication Pursuant to Article 94(3) EPC Dated Dec. 27, 2010 From the European Patent Office Re.: Application No. 07736144.2.
Response Dated Dec. 28, 2010 to Official Action of Sep. 29, 2010 From the US Patent and Trademark Office Re.: U.S. Appl. No. 11/922,913.
Communication Pursuant to Article 94(3) EPC Dated Mar. 2, 2011 From the European Patent Office Re. Application No. 07827148.3.
Official Action Dated Feb. 15, 2011 From the US Patent and Trademark Office Re.: U.S. Appl. No. 11/922,913.
Communication Pursuant to Article 94(3) EPC Dated Jun. 6, 2011 From the European Patent Office Re.: Application No. 07736144.2.
Communication Pursuant to Article 94(3) EPC Dated May 23, 2011 From the European Patent Office Re. Application No. 10153226.5.
Enguehard-Gueiffier et al. "2- [(4-Phenylpiperazin-l-yl)Methyl]Imidazole(Di)Azines as Selective D4-Ligands. Induction of Penile Erection by 2-[4-(2-Methoxyphenyl)Piperazin-1-Ylmethyl]Imidazo[1,2-a]Pyridine (PIP3EA), A Potent and Selective D4 Partial Agonist", Journal of Medicinal Chemistry, 49: 3938-3947, 2006.
Testa et al. "Introduction: Metabolic Hydrolysis and Prodrug Design. Classification, Localization, and Some Physiological Roles of Hydrolytic Enzymes. The Hydrolysis of Carboxylic Acid Esters", Hydrolysis in Drug and Prodrug Metabolism, Helvetica Chimica Acta, Chap.1, 2, 7: 1-46, 370-387, 2003.
Advisory Action Before the Filing of an Appeal Brief Dated Apr. 26, 2011 From the US Patent and Trademark Office Re.: U.S. Appl. No. 11/922,913.
Response Dated Mar. 24, 2011 to European Search Report and the European Search Opinion of Aug. 20, 2010 From the European Patent Office Re. Application No. 10153226.5.
Response Dated Apr. 13, 2011 to Communication Pursuant to Article 94(3) EPC of Dec. 27, 2010 From the European Patent Office Re.: Application No. 07736144.2.
Response Dated Apr. 13, 2011 to Official Action of Feb. 15, 2011 From the US Patent and Trademark Office Re.: U.S. Appl. No. 11/922,913.
Response Dated Apr. 26, 2011 to Communication Pursuant to Article 94(3) EPC of Dec. 27, 2010 From the European Patent Office Re.: Application No. 07736144.2.
Official Action Dated Aug. 25, 2011 From the US Patent and Trademark Office Re.: U.S. Appl. No. 11/922,913.
Response Dated Sep. 26, 2011 to Communication Pursuant to Article 94(3) EPC of Jun. 6, 2011 From the European Patent Office Re.: Application No. 07736144.2.
Response Dated Sep. 14, 2011 to Communication Pursuant to Article 94(3) EPC of May 23, 2011 From the European Patent Office Re. Application No. 10153226.5.
Response Dated Jun. 29, 2011 to Communication Pursuant to Article 94(3) EPC Dated Mar. 2, 2011 From the European Patent Office Re. Application No. 07827148.3.
Communication Pursuant to Article 94(3) EPC Dated Oct. 18, 2011 From the European Patent Office Re.: Application No. 07736144.2.

* cited by examiner

HETEROTRICYCLIC COMPOUNDS AS SEROTONERGIC AND/OR DOPAMINERGIC AGENTS AND USES THEREOF

RELATED APPLICATIONS

This Application is a National Phase of PCT Patent Application No. PCT/IL2007/001174 having International filing date of Sep. 24, 2007, which is a continuation-in-part of PCT Patent Application No. PCT/IL2007/000404 filed on Mar. 28, 2007 which claims the benefit of priority of U.S. Provisional Application Nos. 60/879,531, filed on Jan. 10, 2007 and 60/786,379, filed on Mar. 28, 2006. The contents of the above Applications are all incorporated herein by reference.

FIELD AND BACKGROUND OF THE INVENTION

The present invention relates to the field of pharmacology and, more particularly, to heterocyclic compounds and their use in the treatment of medical conditions associated with the serotonergic system and/or dopaminergic system, including, for example, sexual disorders and various CNS diseases and disorders.

Erectile dysfunction (ED), the most common sexual arousal disorder, involves partial or complete failure to attain or maintain a penile erection adequately for intercourse. Erectile dysfunction is a very common problem, affecting from about 40 to 60 percents of men at some time in their life, and about 52 percents of men between 40 and 70 years old.

Penile erection occurs when blood vessels in the penis, particularly in the corpus cavernosum, become filled with large volumes of blood, causing an enlargement and stiffening of the organ. In response to stimuli from the cerebral cortex and/or the parasympathetic nervous system, nitric oxide is released in penile arteries. Nitric oxide causes the smooth muscle in arteries to relax by activating guanylyl cyclase, increasing the concentration of cyclic guanosine monophosphate (cGMP), which activates protein kinase G. The relaxation of the arterial smooth muscle causes the arteries to expand, increasing the volume of blood flowing through the arteries. The increased volume of blood entering the penis leads to an erection. In women, clitoral erection is caused by an analogous mechanism.

The biological effect of nitric oxide is limited by phosphodiesterases (PDEs) which hydrolyze cGMP Inhibition of PDEs increases the levels of cGMP induced by nitric oxide, thereby magnifying the effects of nitric oxide.

PDE5, first purified and characterized from rat (Francis and Corbin, 1988), is very abundant in vascular smooth muscle cells and appears to play a significant role in modulating smooth muscle tone in general and penile corpus cavernosal smooth muscle tone in particular (Beavo, 1998; Moreland and Goldstein, 1995). Selective inhibitors of PDE5 have therefore been suggested for inducing penile (and clitoral) erection by raising cGMP levels (Tenet et al., 1996).

The principal currently available drugs belonging to the PDE5 inhibitors family are tadalafil (Cialis™), vardenafil (Levitra™) and sildenafil (Viagra™), the most famous one being Viagra™ (sildenafil).

Although sildenafil is considered a selective inhibitor of PDE5, it has long been recognized that it effects on other body organs and hence its use is associated with several adverse side effects such as nausea, headache, and cutaneous flushing. These clinically significant adverse effects are thought to be due to nonspecific inhibition of other PDEs exhibited by this compound (Beavo, 1998; Moreland and Goldstein, 1995).

In addition to PDE5, experimental data indicate that several neurotransmitters and neuropeptides in the central nervous system are involved in the control of penile erection and sexual behavior, one such prominent neurotransmitter being dopamine (Melis and Argiolas, 1995; Andersson, 2001). In contrast to PDE5 inhibition, which directly affects the blood vessels in the penis, dopamine is involved in the regulation of penile activity by the central nervous system.

Dopamine is one of the key mediators in the CNS and is involved in a variety of physiological functions, including sexual behavior, cognition, motor coordination, cardiovascular control, reward and hormonal regulation. Dopamine receptors in mammalian tissues have been classified as D1-like (D1 and D5) and D2-like (D2, D3, and D4) (Missale, 1998). It has been shown that several dopamine receptor agonists such as apomorphine, quinpirole, quinelorane, and (−)-3-(3-hydroxyphenyl)-N-n-propylpiperidine (3-PPP) induce penile erection after systemic administration in mammals (Melis and Argiolas, 1995).

Recent demonstration that apomorphine can facilitate penile erection in erectile dysfunction patients has introduced a new approach to pharmacological correction of erectile dysfunction. It is believed that apomorphine induces penile erection by activating the D4 receptor, although other dopamine receptors may also be involved (Brioni et al., 2004). However, apomorphine is classified as a nonselective agonist because it activates all of the dopamine receptor subtypes (Missale, 1998). It is believed that such non-selectivity is associated with the known emetic action that substantially restricts the practical application of apomorphine. It has therefore been considered desirable to obtain selective D4 agonists.

One selective D4 agonist that was found active in penile erection is ABT-724 (2-[(4-pyridin-2-ylpiperazin-1-yl)methyl]-1H-benzimidazole) (Brioni et al., 2004). Methods of using ABT-724 and related compounds in the treatment of various sexual dysfunctions are disclosed in U.S. Pat. Nos. 7,022,728 and 6,960,589, to Cowart et al. The chemical structures of apomorphine and ABT-724 are presented in Scheme 1 below.

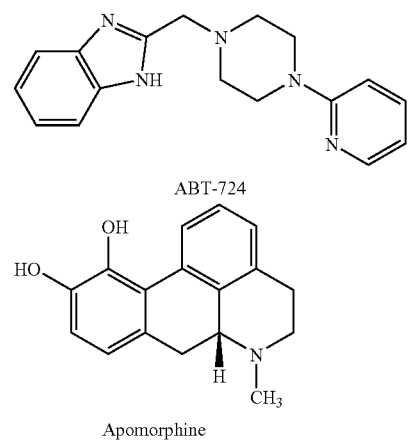

Scheme 1

ABT-724

Apomorphine

Other highly selective dopamine receptor D4 agonists have also been developed. These include, for example, PD-168077 and PIP3EA (Melis et al., 2006), A-412997 (Moreland et al., 2005) and A-381393 (Nakane et al., 2005). These compounds are structurally similar to ABT-724, comprising substituted phenyl groups instead of the pyridine group in ABT-724. In addition, PIP3EA comprises 2-imidazo[1,2-a]pyridine instead of the benzoimidazole in ABT-724, A-412997 and PD-168077 comprise a monocyclic aryl group linked by an amide bond instead of benzoimidazole, and A-412997 comprises piperidine instead of piperazine.

In view of the significance of certain types of dopamine receptors in the control of sexual behavior and penile erection, the discovery of ABT-724 (Brioni et al, 2004; Cowart et al, 2004) and development of other highly selective dopamine receptor D4 agonists (Moreland, 2001) have provided a new strategy for the treatment of erectile dysfunction. A further potential advantage for the use of dopamine receptor agonists is the ability of dopamine receptor agonists, selective D4 agonists in particular, to treat a range of sexual disorders.

An example of another type of sexual disorder is the orgasm disorder, in which orgasm and/or ejaculation are absent or delayed to a degree in which sexual satisfaction is significantly reduced, even in the presence of an adequate erection. One common cause of orgasm disorder is selective serotonin reuptake inhibitor (SSRI) therapy.

Dopamine has been found to regulate ejaculation via D2-like receptors (Wolters & Hellstrom, 2006). Bupropion and amantadine, which stimulate dopamine pathways, have been reported to reverse orgasm disorders (Modell et al., 2000; Balon, 1996), and SSRI-induced orgasm disorders are suspected to be induced by inhibition of dopamine pathways (Alcantara, 1999). PDE5 inhibitors have also been found to reverse SSRI-induced orgasm disorders (Ashton, 2004; Damis et al., 1999).

Another example of a type of sexual disorder is decreased libido, or sexual desire disorder, which is often attributed to aging, psychological disorders such as depression, and medications such as SSRIs.

Dopamine release plays an important role in sexual desire, apparently as part of the general role of dopamine in providing motivation for rewarding activities (Giuliano and Allard, 2001). Consequently, dopamine antagonists tend to reduce sexual desire (Stimmel and Gutierrez, 2006). The D4 receptor in particular has been linked to sexual desire, as well as sexual arousal and function (Ben-Zion et al., 2006).

Another key mediator of the CNS is 5-hydroxytryptamine (5-HT), also known as serotonin. 5-HT is involved in the regulation of anger, aggression, body temperature, moods, sleep, vomiting and appetite, as well as sexuality. Several families of 5-HT receptors are known.

U.S. Pat. No. 3,976,776 discloses compounds comprised of heteroaryl-piperazinylalkyl derivatives of azaspiroalkanediones having tranquilizing and anti-emetic properties. U.S. Pat. No. 4,182,763 discloses a method of treating anxiety by administering buspirone, a heteroaryl-piperazinylalkyl derivative of an azaspiroalkanedione, as a $5\text{-HT}_{1A}$ receptor agonist. Buspirone is commonly used for this purpose. U.S. Pat. No. 5,162,321 discloses 1-naphthyl-piperazinyl alkyl derivatives, including derivatives of azaspiroalkanediones, for use as $5\text{-HT}_{1A}$ receptor ligands, and methods of using such ligands to treat migraine, depression, anxiety, schizophrenia, stress, pain and hypertension.

Buspirone has also been disclosed by U.S. Pat. No. 4,640,921 to effectively treat sexual dysfunction in both male and female subjects. However, buspirone causes numerous side effects, most frequently vertigo, headaches, nervousness, agitation, light-headedness and nausea. In addition, the effect of buspirone is drastically increased by grapefruit consumption, leading to the danger of overdosing.

The chemical structure of buspirone is presented in Scheme 2 below:

Scheme 2

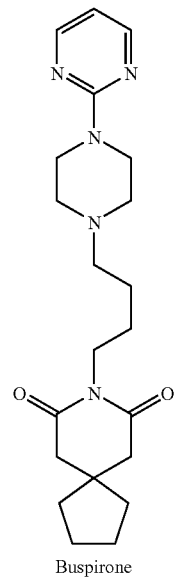

Buspirone

As the $5\text{-HT}_{1A}$ receptor is localized to the CNS, it is believed that $5\text{-HT}_{1A}$ receptor activation alleviates sexual dysfunction by regulating the CNS, similar to the mechanism of dopamine receptor activation.

WO/2005/007166, which is incorporated by reference as if fully set forth herein, teaches the use of PDE-5 inhibitors, in combination with $5\text{HT}_{1A}$ agonists for the treatment of sexual dysfunction, particularly female sexual arousal disorder (FSAD) with concomitant hypoactive sexual desire disorder (HSDD).

Additional indications which have been associated with modulation, activation in particular, of the $5\text{-HT}_{1A}$ receptor include, for example, disorders of the outer retina (see, WO 2001/070222); CNS disorders such as depression, anxiety, neurodegenerative diseases, panic, alcohol and drug addiction, sleep disorders, cognitive disorders, Alzheimer's disease, Parkinson's disease and schizophrenia (see, for example, WO 2004/041815, WO 2003/078420 and WO 2000/035878); and neuronal stem cell differentiation (see, for example, WO 2002/102988). All of the aforementioned publications are incorporated by reference as if fully set forth herein.

Thus, the art teaches agents that act via the dopamine pathway, as well as agents that act via the 5-HT pathway, for treating medical conditions such as sexual disorders and related disorders, as well as CNS disorders such as anxiety and related mood disorder. The clinical effect of most of these agents, however, has not been practiced yet, and, moreover, the utilization of most of these agents is associated with adverse side effects, mostly stemming from the non-selectively thereof.

SUMMARY OF THE INVENTION

The present inventors have now successfully prepared and practiced novel heterotricyclic compounds, which exhibit a serotonergic and/or dopaminergic activity and hence can be beneficially utilized in the treatment of a variety of medical conditions associated with these activities. In some embodiments of the invention, these heterotricyclic compounds are beneficially characterized as capable of selectively activating a D4 dopamine receptor and/or a $5HT_{1A}$ serotonine receptor, and hence can be utilized in the treatment of conditions associated with activating these receptors, preferably while being devoid of adverse side effects.

Thus, according to an aspect of some embodiments of the present invention there is provided a compound having the general Formula I:

A-B-D     Formula I or a pharmaceutically acceptable salt thereof,
wherein:

A is selected from the group consisting of a moiety having general Formula II and a moiety having general Formula III:

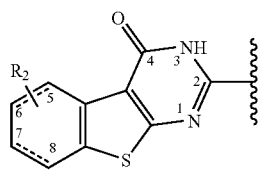

Formula II

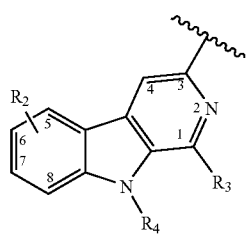

Formula III

B is a moiety selected from the group consisting of:

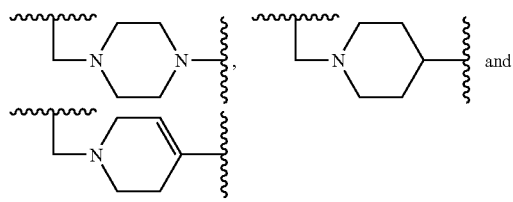

and

D is a moiety selected from the group consisting of:

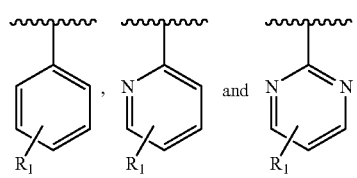

whereas:
a dashed line denotes a saturated or non-saturated bond; and
$R_1$-$R_4$ are each independently selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

In one embodiment, $R_2$-$R_4$ are each hydrogen.

In one embodiment, A is the moiety having general Formula II.

In one embodiment, each of the dashed lines denotes a saturated bond.

In one embodiment, B is

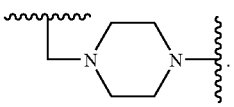

In one embodiment, D is

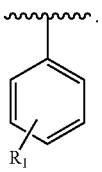

In one embodiment, $R_1$ is selected from the group consisting of hydroxy and alkoxy.

In one embodiment, the compound is selected from the group consisting of B-92; B-94; and B-95 (see, Table 1).

In one embodiment, B is

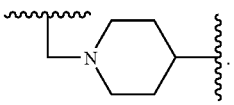

In one embodiment, the compound is B-93 (see, Table 1).

In one embodiment, the dashed line between a carbon atom in position 6 and a carbon atom in position 7 is a saturated bond.

In one embodiment, B is

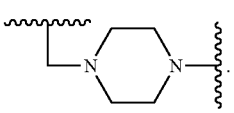

In one embodiment, D is

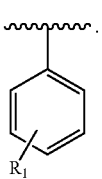

In one embodiment, $R_1$ is selected from the group consisting of hydrogen, hydroxy and alkoxy.

In one embodiment, the compound is selected from the group consisting of: C1; C2; C3; C4; C5; and C6 (see, Table 1).

In one embodiment, the compound is C9 (see, Table 1).

In one embodiment, B is

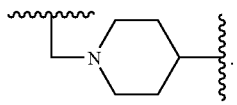

In one embodiment, the compound is C7 (see, Table 1).

In one embodiment, B is

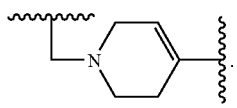

In one embodiment, the compound is C8 (see, Table 1).

In one embodiment, each of the dashed lines is an unsaturated bond.

In one embodiment, B is

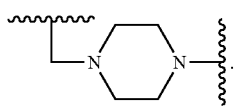

In one embodiment, D is

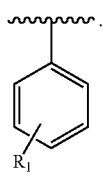

In one embodiment, $R_1$ is selected from the group consisting of hydrogen, halo, hydroxy, and alkoxy.

In one embodiment, the compound is selected from the group consisting of: C10; C11; C13; C14; C15; C16; and C17 (see, Table 1).

In one embodiment, the compound is C12 (see, Table 1).

In one embodiment, the compound is C20 (see, Table 1).

In one embodiment, B is

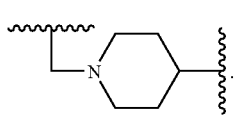

In one embodiment, the compound is C18 (see, Table 1).

In one embodiment, B is

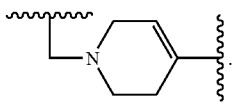

In one embodiment, the compound is C19 (see, Table 1).

In one embodiment, A is the moiety having general Formula III.

In one embodiment, B is

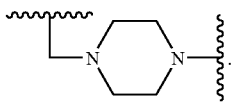

In one embodiment, D is

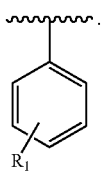

In one embodiment, $R_1$ is selected from the group consisting of hydrogen, hydroxy, and alkoxy.

In one embodiment, the compound is selected from the group consisting of: B-96; B-97; B-98; and B-99 (see, Table 1).

In one embodiment, the compound is capable of modulating an activity of a dopamine receptor.

In one embodiment, the modulating comprises activating a dopamine receptor.

In one embodiment, the compound is characterized as selectively modulating an activity of a D4 dopamine receptor.

In one embodiment, the compound is capable of modulating an activity of a 5-HT receptor.

In one embodiment, the modulating comprises activating a 5-HT receptor.

In one embodiment, the compound is characterized as selectively modulating an activity of a $5-HT_1$ dopamine receptor.

In one embodiment, the $5-HT_1$ receptor is a $5-HT_{1A}$ receptor.

In one embodiment, the compound is capable of modulating an activity of a dopamine receptor and of modulating an activity of a 5-HT receptor.

In one embodiment, the modulating an activity of a dopamine receptor comprises activating an activity of a dopamine receptor.

In one embodiment, the compound is characterized as selectively modulating an activity of a D4 dopamine receptor.

In one embodiment, the modulating an activity of a 5-HT receptor comprises activating the 5-HT receptor.

In one embodiment, the compound is characterized as selectively modulating an activity of a $5-HT_1$ dopamine receptor.

In one embodiment, the $5-HT_1$ receptor is a $5-HT_{1A}$ receptor.

According to an aspect of some embodiments of the present invention there is provided a pharmaceutical composition comprising, as an active ingredient, the compound as described herein and a pharmaceutically acceptable carrier.

In one embodiment, the pharmaceutical composition is packaged in a packaging material and identified in print, in or on the packaging material, for use in the treatment of a sexual disorder.

In one embodiment, the pharmaceutical composition is packaged in a packaging material and identified in print, in or on the packaging material, for use in the treatment of a condition in which activating a dopamine receptor is beneficial.

In one embodiment, the pharmaceutical composition is packaged in a packaging material and identified in print, in or on the packaging material, for use in the treatment of a condition in which activating a 5-$HT_1$ receptor is beneficial In one embodiment, the pharmaceutical composition is packaged in a packaging material and identified in print, in or on the packaging material, for use in the treatment of a condition in which activating a dopamine receptor and activating a 5-$HT_1$ receptor is beneficial.

In one embodiment, the pharmaceutical composition is packaged in a packaging material and identified in print, in or on the packaging material, for use in the treatment of a condition selected from the group consisting of a sexual disorder, Parkinson's disease, attention deficit hyperactivity disorder (ADHD), female sexual arousal disorder (FSAD), hypoactive sexual desire disorder (HSDD); a CNS (central nervous system disorder, including, anxiety, depression, migraine, schizophrenia, stress, pain, hypertension, a neurodegenerative disease, panic, alcohol and drug addiction, a sleep disorder, a cognitive disorder, Alzheimer's disease, psychosis and dyskinesia; and an outer retina disorder.

In one embodiment, the pharmaceutical composition is packaged in a packaging material and identified in print, in or on the packaging material, for use in activation and/or differentiation of neuronal stem cells, and/or in the treatment of a condition associated with activation and/or differentiation of neuronal stem cells.

According to an aspect of some embodiments of the present invention there is provided a use of the compound as described herein in the manufacture of a medicament for treating a sexual disorder.

According to an aspect of some embodiments of the present invention there is provided a method of treating a sexual disorder, the method comprising administering to a subject in need thereof the compound as described herein.

In one embodiment, the sexual disorder is selected from the group consisting of decreased libido, orgasm disorder and erectile dysfunction.

According to an aspect of some embodiments of the present invention there is provided a method of activating a dopamine receptor, the method comprising contacting the dopamine receptor with an effective amount of the compound as described herein.

In one embodiment, the method is for treating a medical condition in which activating a dopamine receptor is beneficial.

According to an aspect of some embodiments of the present invention there is provided use of the compound as described herein as an agonist of a dopamine receptor.

According to an aspect of some embodiments of the present invention there is provided a use of the compound as described herein in the manufacture of a medicament for treating a condition in which activating a dopamine receptor is beneficial.

In one embodiment, the condition is selected from the group consisting of a sexual disorder, Parkinson's disease, and attention deficit hyperactivity disorder.

According to an aspect of some embodiments of the present invention there is provided a method of activating a 5-$HT_1$ receptor, the method comprising contacting the 5-$HT_1$ receptor with an effective amount of the compound as described herein.

In one embodiment, the method is for treating a medical condition in which activating a 5-$HT_1$ receptor is beneficial.

According to an aspect of some embodiments of the present invention there is provided a use of the compound as described herein as an agonist of a 5-$HT_1$ receptor.

According to an aspect of some embodiments of the present invention there is provided a use of the compound as described herein in the manufacture of a medicament for treating a condition in which activating a 5-$HT_1$ receptor is beneficial.

In one embodiment, the condition is selected from the group consisting of a female sexual arousal disorder (FSAD), hypoactive sexual desire disorder (HSDD); a CNS (central nervous system) disorder, including, anxiety, depression, migraine, schizophrenia, stress, pain, hypertension, a neurodegenerative disease, panic, alcohol and drug addiction, a sleep disorder, a cognitive disorder, Alzheimer's disease, psychosis and dyskinesia; and an outer retina disorder.

According to an aspect of some embodiments of the present invention there is provided a use of the compound as described herein in the manufacture of a medicament for activation and/or differentiation of neuronal stem cells, and/or for the treatment of a condition associated with activation and/or differentiation of neuronal stem cells.

According to an aspect of some embodiments of the present invention there is provided a method of activating a 5-$HT_1$ receptor and a dopamine receptor, the method comprising contacting the 5-$HT_1$ receptor and the dopamine receptor with an effective amount of the compound as described herein, the method being for treating a medical condition in which activating a dopamine receptor and a 5-$HT_1$ receptor is beneficial.

According to an aspect of some embodiments of the present invention there is provided a use of the compound as described herein in the manufacture of a medicament for treating a condition in which activating a 5-$HT_1$ receptor and a dopamine receptor is beneficial.

In one embodiment, the 5-$HT_1$ receptor is a 5-$HT_{1A}$ receptor, and the compound is characterized as a selective agonist of the 5-$HT_{1A}$ receptor.

In one embodiment, the dopamine receptor is a D4 receptor, and the compound is characterized as a selective agonist of the D4 receptor.

In one embodiment, the condition is a sexual disorder.

According to an aspect of some embodiments of the present invention there is provided a method of treating a medical condition selected from the group consisting of a sexual disorder, Parkinson's disease, attention deficit hyperactivity disorder (ADHD), female sexual arousal disorder (FSAD), hypoactive sexual desire disorder (HSDD); a CNS (central nervous system disorder, including, anxiety, depression, migraine, schizophrenia, stress, pain, hypertension, a neurodegenerative disease, panic, alcohol and drug addiction, a sleep disorder, a cognitive disorder, Alzheimer's disease, psychosis and dyskinesia; and an outer retina disorder, the method comprising administering to a subject in need thereof a therapeutically effective amount of the compound as described herein.

According to an aspect of some embodiments of the present invention there is provided a use of the compound as described herein in the manufacture of a medicament for treating a condition selected from the group consisting of a sexual disorder, Parkinson's disease, attention deficit hyperactivity disorder (ADHD), female sexual arousal disorder (FSAD), hypoactive sexual desire disorder (HSDD); a CNS (central nervous system disorder, including, anxiety, depression, migraine, schizophrenia, stress, pain, hypertension, a neurodegenerative disease, panic, alcohol and drug addiction, a sleep disorder, a cognitive disorder, Alzheimer's disease, psychosis and dyskinesia; and an outer retina disorder.

According to an aspect of some embodiments of the present invention there is provided a method of activating and/or differentiating neuronal stem cells, the method comprising contacting the cells with the compound as described herein.

According to an aspect of some embodiments of the present invention there is provided a method of treating a condition is which activation and/or differentiation of neuronal stem cells is beneficial, the method comprising administering to a subject in need thereof a therapeutically effective amount of the compound as described herein According to an aspect of some embodiments of the present invention there is provided a use of the compound as described herein, in the manufacture of a medicament for treating a condition in which activation and/or differentiation of neuronal stem cells is beneficial.

According to an aspect of some embodiments of the present invention there is provided a process of preparing the compound as described herein, the process comprising:

reacting a compound having the general Formula:

wherein X is a leaving group,
and a compound selected from the group consisting of:

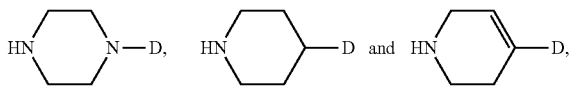

thereby obtaining the compound having the general Formula I.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a", "an" and "the" include plural references unless the context clearly dictates otherwise. For example, the term "a protein" or "at least one protein" may include a plurality of proteins, including mixtures thereof.

As used herein the term "about" refers to ±10%.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein the term "about" refers to ±10%.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF THE PREFERRED EMBODIMENTS

Figure 1:
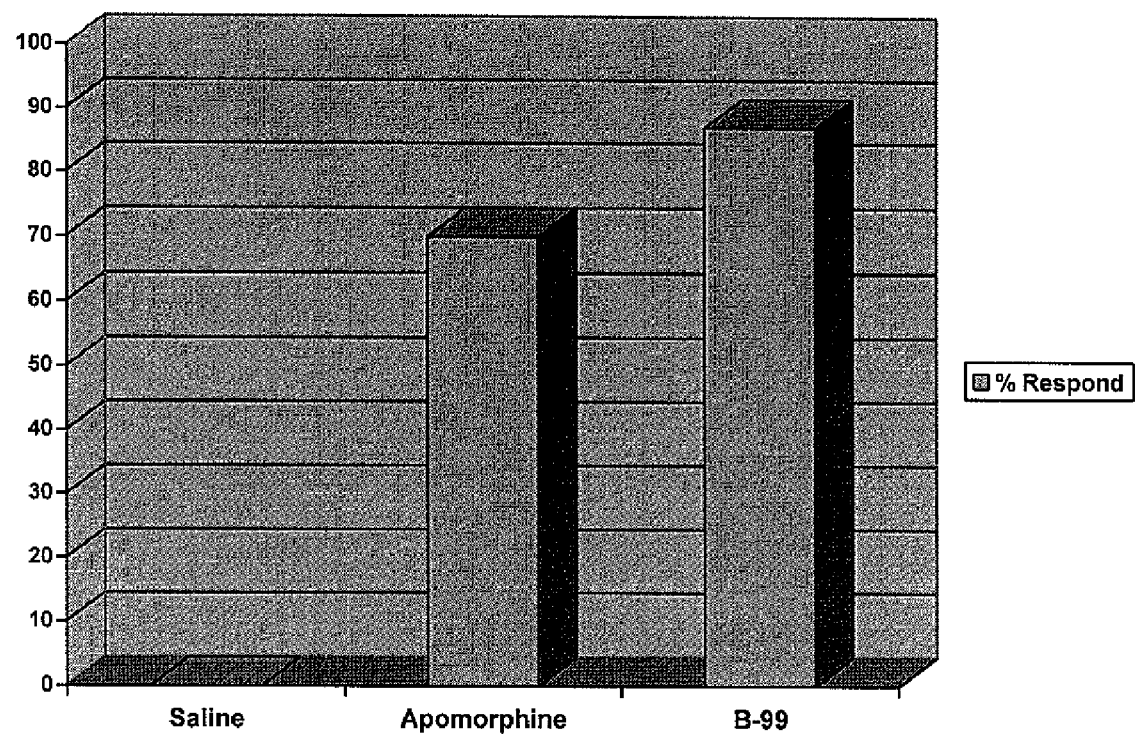
FIG. 1 is a bar graph presenting the results obtained in in vivo studies in rates, and demonstrating the superior effect of B-99, an exemplary compound according to the present embodiment, as compared to apomorphine, in penile erection test.

The present invention is of novel heterocyclic compounds, which are designed to exhibit a dopamine receptor (preferably a D4 receptor) agonistic activity, and/or a 5-HT receptor (preferably 5-$HT_{1A}$) agonistic activity, and hence can be beneficially utilized in the treatment of medical conditions associated with the serotonergic system and/or dopaminergic system, including, for example, sexual disorders and various CNS disorders.

The principles and operation of embodiments of the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, growing evidence suggests that D4 dopamine receptor agonists have a role in the treatment of erectile dysfunction, as well as other sexual disorders, such as orgasm disorder and sexual desire disorder. 5-HT$_{1A}$ serotonin receptors have been found to have a similar role.

PCT/IL2007/000404, filed Mar. 28, 2007, by the present assignee, which is incorporated by reference as if fully set forth herein, discloses novel compounds which exhibit D4 dopamine receptor agonistic activity and/or PDE-5 inhibition activity.

The present inventors have now designed and successfully practiced novel compounds, which exhibit a selective agonistic activity of a dopamine receptor and/or a selective agonistic activity of a serotonine receptor. These compounds were found to exhibit a potent activity in treating erectile dysfunction, while being devoid of common adverse side effects associated with currently known dopamine and/or serotonine agonists.

The compounds described herein are also referred to as heterocyclic compounds and can be collectively represented by the general Formula I:

A-B-D    Formula I wherein:

A is selected from the group consisting of a moiety having general Formula II and a moiety having general Formula III:

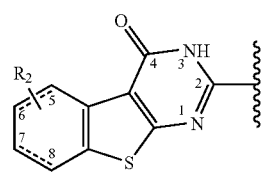

Formula II

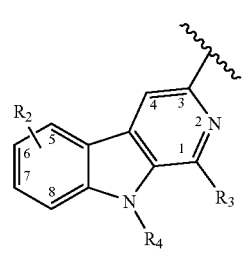

Formula III

B is a moiety selected from the group consisting of:

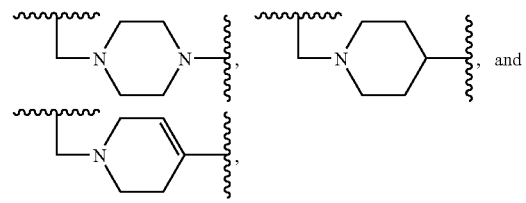

D is a moiety selected from the group consisting of:

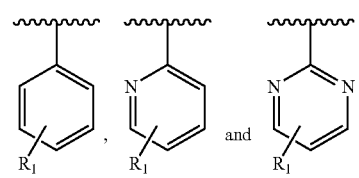

whereas:

a dashed line denotes a saturated or non-saturated bond; and $R_1$-$R_4$ are each independently selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

As used herein, the term "moiety" describes a portion of a chemical group that is linked to one or more other moieties, via covalent bond(s), whereby the linkage is effected via the position(s) marked by a curved line.

The B moiety is positioned such that a nitrogen atom in the B moiety is linked by a methylene group bound thereto to the A moiety, whereas the other end of the B moiety is linked to the D moiety.

It will be appreciated by one of skills in the art that the feasibility of each of the substituents ($R_1$-$R_4$) to be located at the indicated positions depends on the valency and chemical compatibility of the substituent, the substituted position and other substituents. Hence, the present invention is aimed at encompassing all the feasible substituents for any position.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, guanyl, guanidine and hydrazine.

The alkyl group is an end group, as this phrase is defined hereinabove, wherein it is attached to a single adjacent atom.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, guanyl, guanidine and hydrazine.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, guanyl, guanidine and hydrazine.

As used herein, the term "amine" describes both a —NRxRy group and a —NRx- group, wherein Rx and Ry are each independently hydrogen, alkyl, cycloalkyl, aryl, as these terms are defined herein.

The amine group can therefore be a primary amine, where both Rx and Ry are hydrogen, a secondary amine, where Rx is hydrogen and Ry is alkyl, cycloalkyl or aryl, or a tertiary amine, where each of R' and R" is independently alkyl, cycloalkyl or aryl.

Alternatively, Rx and Ry can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, carboxy, thiocarbamate, urea, thiourea, carbamate, amide, guanyl, guanidine and hydrazine.

The term "halide" and "halo" describes fluorine, chlorine, bromine or iodine.

The term "haloalkyl" describes an alkyl group as defined above, further substituted by one or more halide(s). Accordingly, the term "trihaloalkyl" describes an alkyl group, as defined above, further substituted by three halides.

The term "sulfate" describes a —O—S(=O)$_2$—ORx group, where $R_X$ is as defined hereinabove.

The term "thiosulfate" describes a —O—S(=S)(=O)—ORx group, where Rx is as defined hereinabove.

The term "sulfite" describes an —O—S(=O)—O—Rx group, where $R_X$ is as defined hereinabove.

The term "thiosulfite" describes a —O—S(=S)—O—Rx group, where $R_X$ is as defined hereinabove.

The term "sulfinate" describes a —S(=O)—ORx group, where $R_X$ is as defined hereinabove.

The term "sulfoxide" or "sulfinyl" describes a —S(=O)—Rx group, where Rx is as defined hereinabove.

The term "sulfonate" or "sulfonyl" describes a —S(=O)$_2$—Rx group, where Rx is as defined herein.

The term "sulfonamide", as used herein, encompasses both S-sulfonamides and N-sulfonamides.

The term "S-sulfonamide" describes a —S(=O)$_2$—NRxRy group, with Rx and $R_Y$ as defined herein.

The term "N-sulfonamide" describes an RxS(=O)$_2$—NR$_Y$— group, where Rx and $R_Y$ are as defined herein.

The term "disulfide" refers to a —S—SRx group, where Rx is as defined herein.

The term "carbonyl" or "carbonate" as used herein, describes a —C(=O)—Rx group, with Rx as defined herein.

The term "thiocarbonyl" as used herein, describes a —C(=S)—Rx group, with Rx as defined herein.

The term "oxo", as used herein, describes an =O group.

The term "oxime" describes a =N—OH group.

The terms "hydroxy" and "hydroxyl" describe a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "ether" describes groups in which a carbon atom in an alkyl, cycloalkyl, aryl or heteroaryl is attached to an alkoxy or aryloxy group.

The term "thioether" describes groups in which a carbon atom in an alkyl, cycloalkyl, aryl or heteroaryl is attached to a thioalkoxy or thioaryloxy group.

The terms "cyano" and "nitrile" describe a —C≡C group.

The term "isonitrile" describes a —N≡C group.

The term "isocyanate" describes an —N=C=O group.

The term "nitro" describes an —NO$_2$ group.

The term "acyl halide" describes a —(C=O)—Rz group wherein Rz is halide, as defined hereinabove.

The term "azo" or "diazo" describes an —N=NR' group, with R' as defined hereinabove.

The term "peroxo" describes an —O—ORx group, with Rx as defined hereinabove.

The term "carboxy", as used herein, encompasses both C-carboxy and O-carboxy groups.

The term "C-carboxy" describes a —C(=O)—ORx group, where Rx is as defined herein.

The term "O-carboxy" describes a —OC(=O)—Rx group, where R' is as defined herein.

The term "thiocarboxy", as used herein, encompasses both C-thiocarboxy and O-thiocarboxy groups.

The term "C-thiocarboxy" describes a —C(=S)—ORx group, where Rx is as defined herein.

The term "O-thiocarboxy" describes a —OC(=S)Rx group, where Rx is as defined herein.

The term "urea" describes a —NRxC(=O)—NRyRw group, where Rx and Ry are as defined herein and Rw is as defined herein for $R_X$ and Ry.

The term "thiourea" describes a —NRx-C(=S)—NRyRw group, with Rx, Ry and Ry as defined herein.

The term "amide", as used herein, encompasses both C-amides and N-amides.

The term "C-amide" describes a —C(=O)—NRxRy group, where Rx and Ry are as defined herein.

The term "N-amide" describes an RxC(=O)—NRy- group, where Rx and Ry are as defined herein.

The term "carbamyl" or "carbamate", as used herein, encompasses both N-carbamates and O-carbamates.

The term "N-carbamate" describes an RyOC(=O)—NRx- group, with Rx and Ry as defined herein.

The term "O-carbamate" describes an —OC(=O)—NRxRy group, with Rx and Ry as defined herein.

The term "thiocarbamyl" or "thiocarbamate", as used herein, encompasses both O-thiocarbamates and N-thiocarbamates.

The term "O-thiocarbamate" describes a —OC(=S)—NRxRy group, with Rx and Ry as defined herein.

The term "N-thiocarbamate" describes an RyOC(=S) NRx- group, with Rx and Ry as defined herein.

As used herein, the term "epoxide" describes a

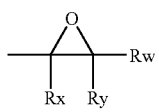

group, where Rx, Ry and Rw are as defined herein.

As used herein, the term "thiirane" describes a group that is equivalent to an epoxide, wherein the oxygen atom of the epoxide is replaced with a sulfur atom.

As used herein, the term "aziridine" describes a group that is equivalent to an epoxide, wherein the oxygen atom of the epoxide is replaced with a nitrogen atom, and the nitrogen atom binds, in addition to two adjacent carbon atoms, Rq, wherein Rq is defined according to the same definition as Rx.

The term "guanyl" describes a RxRyNC(=N)— group, where Rx and Ry are as defined herein.

The term "nitroso" describes a —N=O group.

The term "guanidine" describes a —RxNC(=N)—NRyRw group, where Rx, Ry and Rw are as defined herein.

The term "hydrazine", as used herein, describes a —NRx-NRyRw group, with Rx, Ry, and Rw as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. Representative examples are piperidine, piperazine, tetrahydrofurane, tetrahydropyrane, morpholino and the like.

As presented in Formula I, the compounds described herein comprise a heterotricyclic moiety, referred to therein as "A", linked to a cyclic amine moiety via a methylene group, the cyclic amine with methylene moiety being referred to herein as "B", which is linked to an aryl or heteroaryl moiety referred to herein as "D".

As used herein, the phrase "heterotricyclic moiety" describes a moiety that comprises three fused rings, wherein each ring shares two atoms with at least one other ring, and wherein at least one ring comprises an atom that is not a carbon atom.

As used herein, the phrase "cyclic amine" describes a cyclic moiety that comprises at least one nitrogen atom therewithin.

According to one embodiment of the present invention, A is a heterotricyclic moiety having general Formula II above. Such compounds are collectively referred to herein interchangeably as compounds of Family 1 or Family 1 compounds.

The heterotricyclic moiety (the A moiety) of Family 1 compounds comprises a 3H-pyrimidin-4-one ring, fused to a thiophene ring, which in turn is fused to a six-membered ring. The six-membered ring comprises two optional unsaturated bonds, depicted as dashed lines in Formula II above. Thus, the six-carbon ring may comprise 0, 1 or 2 saturated bonds. In embodiments wherein the six-carbon ring comprises 1 saturated bond, the saturated bond may be any one of the two bonds depicted as optional saturated bonds in Formula II. Preferably, the saturated bond is in the location of the optional unsaturated bond that is between a carbon atom that is in position 6 and a carbon that is in position 7.

The heterotricyclic moiety of Family 1 compounds may be substituted or unsubstituted at the six-membered carbon ring (see, $R_2$ in Formula II above). Preferably, the heterotricyclic moiety is unsubstituted, such that $R_2$ is hydrogen.

According to another embodiment of the present invention, A is a heterotricyclic moiety having general Formula III above. Such compounds are collectively referred to herein interchangeably as compounds of Family 2 or Family 2 compounds.

The heterotricyclic moiety of Family 2 compounds may be substituted or unsubstituted. Substitution may be at 3 sites (see, $R_2$, $R_3$ and $R_4$ in Formula III). Substitution may also be at any 1 or 2 sites only. Preferably, the heterotricyclic moiety is unsubstituted, such that $R_2$, $R_3$ and $R_4$ are each hydrogen.

According to embodiments of the present invention, the end group D is an aryl or heteroaryl group, being phenyl, pyridin-2-yl or pyrimidin-2-yl, wherein each of the aforementioned end groups may be substituted or unsubstituted.

Thus, in one embodiment, D is pyridin-2-yl or pyrimidin-2-yl, being substituted or unsubstituted. Preferably, the heteroaryl is unsubstituted, such that $R_1$ is hydrogen.

In another embodiment, D is a substituted or unsubstituted phenyl.

In a preferred embodiment of the present invention, $R_1$ is selected from the group consisting of hydrogen, hydroxy, alkoxy and halogen. Exemplary alkoxy groups for use in embodiments of the present invention include methoxy, ethoxy and propoxy. An exemplary halogen is chloro.

In a preferred embodiment of the present invention, the hydroxy substituent is positioned on the aryl or heteroaryl of D at an ortho or meta position with respect to B.

In a preferred embodiment of the present invention, the alkoxy or halogen substituent is positioned on the aryl or heteroaryl of D at an ortho position with respect to B.

Exemplary compounds according to the present embodiments are presented in Table 1 hereinbelow.

Each of the compounds described herein can further be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of the present embodiments, preferably, a pharmaceutically acceptable salt of the compounds described herein is an acid addition salt which includes a cyclic amine, as described herein, in which the amine is in a form of a quaternary ammonium ion, and a counter ion, derived from the selected acid, that forms a pharmaceutically acceptable salt.

Depending on the stoichiometric proportions between the base (the amine) and the acid in the salt, the acid additions salts can be either mono addition salts or poly addition salts.

The phrase "mono addition salt", as used herein, refers to a salt in which the stoichiometric ratio between the acid anion and amine cation is 1:1, such that the acid addition salt includes one molar equivalent of the acid per one molar equivalent of the compound.

The phrase "poly addition salt", as used herein, refers to a salt in which the stoichiometric ratio between the acid anion and the amine cation is greater than 1:1 and is, for example, 2:1, 3:1, 4:1 and so on, such that the acid addition salt includes two or more molar equivalents of the acid per one molar equivalent of the compound.

The acid addition salts of the compounds described herein are therefore complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono acid addition salt or a poly acid addition salt, as these terms are defined hereinabove, and can further be in a form of a hydrate thereof, as defined hereinbelow.

Further, each of the compounds described herein, including the salts thereof, can be in a form of a prodrug, a solvate or a hydrate thereof.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as any isomorph thereof.

According to one embodiment of the present invention, each of the compounds described herein is characterized as being capable of modulating an activity of a dopamine receptor. Preferably, the compound is a dopamine receptor agonist. More preferably, the dopamine agonist is a selective D4 receptor agonist.

As used herein, the phrase "modulating an activity" encompasses increasing an activity and decreasing an activity.

As used herein, the phrase "dopamine receptor" encompasses any subtype of dopamine receptor, including, but not limited to, the D1, D2, D3, D4 and D5 subtypes, except where a specific subtype is referred to. The phrase further encompasses all isoforms and conformers of each subtype.

As used herein, the phrase "D4 receptor" encompasses D4 dopamine receptor, including all isoforms and conformers of thereof.

The term "agonist" with respect to any receptor describes a compound that can bind the receptor, thus acting as a ligand of the receptor, whereby the binding of the compound to the receptor results in activating the receptor.

The phrase "selective agonist" with respect to D4 receptor, describes a compound that binds to a D4 receptor at higher affinity as compared to other subtypes of dopamine receptors (e.g., D2). Preferably, the selectivity of the D4 receptor agonist is determined by measuring the ratio of its binding to D4 and to D2. Such a ratio is preferably 10:1 or more, and can be, for example, 10:1, 20:1, 50:1, 100:1, 200:1 and even 500:1.

The term "activating" with respect to a receptor describes activating a biological pathway that is mediated by the dopamine receptor.

According to another embodiment of the present invention, each of the compounds described herein is characterized as being capable of modulating an activity of a 5-HT receptor (a serotonine receptor). Preferably, the compound is a 5-HT receptor agonist. More preferably, the 5-HT receptor agonist is a selective $5\text{-HT}_1$ receptor agonist. Most preferably, the 5-HT receptor agonist is a selective $5\text{-HT}_{1A}$ receptor agonist.

As used herein, the phrase "5-HT receptor" encompasses a member of any family of 5-HT receptor, including, but not limited to, the $5\text{-HT}_1$, $5\text{-HT}_2$, $5\text{-HT}_3$, $5\text{-HT}_4$, $5\text{-HT}_S$, $5\text{-HT}_6$ and $5\text{-HT}_7$ families, except where a specific family is referred to. The phrase further encompasses all subtypes of each family, and all isoforms and conformers of each subtype.

As used herein, the phrase "5-$HT_1$ receptor" encompasses 5-$HT_1$ serotonin receptor, including all subtypes thereof.

As used herein, the phrase "5-$HT_{1A}$ receptor" encompasses 5-$HT_{1A}$ serotonin receptor, including all isoforms and conformers thereof.

The phrase "selective agonist" with respect to 5-$HT_1$ receptor, describes a compound that binds to a 5-$HT_1$ receptor at higher affinity as compared to other families of 5-HT receptors (e.g., 5-$HT_2$).

The phrase "selective agonist" with respect to 5-$HT_{1A}$ receptor, describes a compound that binds to a 5-$HT_{1A}$ receptor at higher affinity as compared to other subtypes of 5-$HT_1$ receptors (e.g., 5-$HT_{1B}$).

According to a preferred embodiment of the present invention, any of the compounds described herein is characterized as being capable of both modulating an activity of a 5-HT receptor and of modulating a dopamine receptor. Preferably, the modulation of both receptors comprises activation of the 5-HT and dopamine receptors. The compound is preferably a selective 5-$HT_1$ receptor agonist, and more preferably, a selective 5-$HT_{1A}$ receptor agonist. The compound is further preferably a selective D4 receptor agonist.

As implied hereinabove and is further discussed in more detail in the Examples section that follows, the compounds described herein are preferably selected capable of binding, preferably simultaneously, to pharmacophoric binding sites of a dopamine (D4) receptor and a serotonin (5-$HT_{1A}$) receptor, so as to activate the dopamine and serotonin receptors concurrently. As further discussed hereinabove, the binding of the compounds is desirably effected selectively to the D4 and 5-$HT_{1A}$ receptors, thus avoiding adverse side effects.

As used herein, the phrase "binding site" describes a specific site in a receptor that includes one or more reactive groups through which the interactions with the receptor ligand and/or other components can be effected. Typically, the binding site is composed of one or two amino acid residues, whereby the interactions typically involve reactive groups at the side chains of these amino acids.

The interactions of the various functional groups of the compound with the various binding sites of the receptor can be, for example, Van der Waals interactions, electrostatic interactions, hydrogen bonding interactions, hydrophobic interactions, aromatic interactions, π-stacking interactions, and the like, depending on the reactive groups that participate in the interactions and their proximity and orientation to one another.

Exemplary electrostatic interactions include anion-cation interactions and acid-base interactions such as, for example, interactions between ammonium cation and carboxylate anion.

Exemplary hydrogen bonding interactions include interactions between hydrogens of amine, hydroxyl or thiol of one or more component(s) and e.g., oxygen, nitrogen and sulfur atoms of other component(s).

Exemplary hydrophobic interactions include interactions between two or more hydrocarbon moieties such as alkyl, cycloalkyl and aryl.

Exemplary aromatic interactions include interactions between two or more aromatic moieties such as aryls and heteroaryls, which are based on overlap in the aromatized molecular orbitals of the moieties.

Exemplary π-stacking interactions include interactions between two or more moieties that contain π-electrons (e.g., unsaturated moieties), which are based on overlap in the π-orbitals of the moieties.

Being designed capable of acting as serotonin receptor agonists, in particular as a 5-$HT_1$ agonist and/or acting as dopamine receptor agonists, the compounds described herein are particularly suitable for use in the activation of a serotonin receptor and/or a dopamine receptor.

Hence, according another aspect of the present invention there is provided a method of activating a dopamine receptor, particularly a D4 receptor, the method comprising contacting the dopamine receptor with an effective amount of the abovementioned compound.

Further provided is a method of activating a 5-$HT_1$ receptor, particularly a 5-$HT_{1A}$ receptor, the method comprising contacting the 5-$HT_1$ receptor with an effective amount of the abovementioned compound.

Still further provided is a method of activating a 5-$HT_1$ receptor and a dopamine receptor concurrently, particularly a D4 receptor and a 5-$HT_{1A}$ receptor, the method comprising contacting the 5-$HT_1$ receptor and dopamine receptor with an effective amount of the abovementioned compound.

The contacting may be effected in vivo or ex vivo (in vitro).

Further provided are uses of the compounds described herein as agonists of a 5-$HT_1$ receptor and/or of a dopamine receptor.

Being designed capable of acting as serotonin receptor agonists and/or acting as dopamine receptor agonists, the compounds described herein are particularly suitable for use in the treatment of conditions in which these activities are beneficial.

Hence, in another aspect of the invention, there is provided a use of any of the compounds described herein, in the manufacture of a medicament for treating a condition in which the abovementioned activities are beneficial.

Exemplary conditions in which activation of a dopamine receptor is beneficial include a sexual disorder, Parkinson's disease and attention deficit hyperactivity disorder (ADHD).

Exemplary conditions in which activation of a 5-$HT_1$ receptor is beneficial include a sexual disorder, including, for example, female sexual arousal disorder (FSAD) and hypoactive sexual desire disorder (HSDD); CNS (central nervous system disorders, such as anxiety, depression, migraine, schizophrenia, stress, pain, hypertension, neurodegenerative diseases, panic, alcohol and drug addiction, sleep disorders, cognitive disorders, Alzheimer's disease, Parkinson's disease, psychosis, and dyskinesia; and outer retina disorders, including, for example, AMD, RP and other forms of heterodegenerative retinal disease, retinal detachment and tears, macular pucker, ischemia affecting the outer retina, diabetic retinopathy, damage associated with laser therapy (grid, focal, and panretinal) including photodynamic therapy (PDT), trauma, surgical (retinal translocation, subretinal surgery, or vitrectomy) or light-induced iatrogenic retinopathy, and preservation of retinal transplants.

Thus, for example, the compounds described herein may be useful for treatment of any one or more of the following diseases or disorders: anxiety, migraine, outer retina disorders, sexual dysfunctions in general, female sexual arousal disorder (FSAD) in particular, depression, ADHD, schizophrenia, neurodegenerative disorders in general, Alzheimer's disease and Parkinson disease.

In addition, the compounds described herein can be used in the manufacture of a medicament for activation and/or differentiation of neuronal stem cells and for the treatment of any condition associated with these activities.

A sexual disorder is an exemplary condition in which activation of both a dopamine receptor and a 5-$HT_1$ receptor is beneficial.

In a preferred embodiment of the present invention, the 5-HT$_1$ receptor agonist mentioned in the context of the abovementioned methods and uses is characterized as a selective 5-HT$_{1A}$ receptor agonist.

In a preferred embodiment of the present invention, the dopamine receptor agonist mentioned in the context of the abovementioned methods and uses is characterized as a selective D4 receptor agonist.

As discussed hereinabove, sexual dysfunction as an exemplary condition in which both activation of a dopamine receptor and activation of a 5-HT$_1$ receptor can be beneficial.

Hence, in a preferred embodiment of the present invention, there is provided a use of any of the abovementioned compounds in the manufacture of a medicament for treating a sexual disorder.

In another preferred embodiment of the present invention, there is provided a method of treating a sexual disorder, the method comprising administering any of the abovementioned compounds to a subject in need thereof.

Exemplary sexual disorders according to embodiments of the present invention include decreased libido, orgasm disorder, and erectile dysfunction.

As used herein the terms "treating", "treatment" and any grammatical diversion thereof include abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the phrase "sexual disorder", also referred to herein and in the art as "sexual dysfunction" describes a medical condition that is expressed by a difficulty during any stage of the sexual act (which includes desire, arousal, orgasm, and resolution) that prevents the individual or couple from enjoying sexual activity. The medical condition can be associated with a mental malfunction, a physical malfunction and/or can be as a result of a medication, a drug, alcohol, and other external factors.

Sexual disorders are generally classified into the following categories: sexual desire disorders (decreased libido), sexual arousal disorders (e.g., erectile dysfunction), and orgasm disorders (e.g., expressed by delay or absence of orgasm following a normal sexual excitement phase).

The subject is preferably a mammal, more preferably a human.

The methods and uses described herein can optionally be effected by combining the compounds described herein with other agents for treating sexual disorders (e.g., additional active agents that act as 5-HT$_{1A}$ or D4 agonists and/or PDE-inhibitors), or, alternatively, by combining the compounds described herein with, for example, a drug such as SSRI, which is known to cause a sexual dysfunction, in order to reduce or prevent the adverse effect of the drug in this regard.

In any of the methods and uses described herein, the compounds presented herein, can be utilized either per se, or, preferably as a part of a pharmaceutical composition.

Hence, according to another aspect of the present invention, there are provided pharmaceutical compositions, which comprise one or more of the compounds described above and a pharmaceutically acceptable carrier.

As used herein a "pharmaceutical composition" refers to a preparation of one or more of the compounds described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the abovementioned compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the compounds of the invention can be formulated readily by combining the compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds of the present invention and a suitable powder base such as, but not limited to, lactose or starch.

The compounds described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds of the present invention prepared in water-soluble form. Additionally, suspensions of the compounds may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds to allow for the preparation of highly concentrated solutions.

Alternatively, the compounds of the present invention may be in powder form for constitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in a therapeutically effective amount for achieving the intended purpose. More specifically, a "therapeutically effective amount" means an amount of one or more of the compounds of the present invention sufficiently effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from activity assays in animals. For example, a dose can be formulated in animal models to achieve a circulating concentration range that has been shown by activity assays to result in both significant D4 receptor binding and/or activation, and significant 5-$HT_{1A}$ receptor binding and/or activation. Such information can be used to more accurately determine useful doses in humans.

Toxicity and therapeutic efficacy of the compounds described herein can be determined by standard pharmaceutical procedures in experimental animals, e.g., by determining the $EC_{50}$, the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% of the maximal level of D4 receptor and/or 5-$HT_{1A}$ activation. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition, as is detailed hereinabove.

Thus, according to an embodiment of the present invention, depending on the selected compound(s), the pharmaceutical compositions of the present invention are packaged in a packaging material and identified in print, in or on the packaging material, for use in the treatment of a condition in which activation of a dopamine receptor and/or a 5-HT$_1$ are desirable, as described hereinabove. Preferably the condition is a sexual disorder.

In each of the methods, uses and compositions described herein, the compound can optionally be utilized (co-administered or co-formulated) in combination with another active agent.

Such active agents can be, for example, an additional dopamine agonist and/or an additional 5-HT$_1$ agonist, or another active agent known to treat sexual dysfunction, such as a PDE5 inhibitor.

Alternatively, the compounds can be utilized in combination with drugs or other agents that are known to cause a sexual disorder as an adverse side effect thereof (e.g., SSRIs), in order to reduce or prevent the sexual dysfunction caused thereby.

Further according to the present invention there are provided processes for preparing the compounds described herein. These processes are generally effected by reacting a compound having the general Formula:

wherein X is a leaving group,
and a cyclic amine compound selected from the group consisting of:

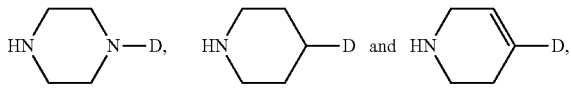

wherein D is as defined for Formula I hereinabove.

The reaction is preferably a nucleophilic reaction, in which an NH in any of the above cyclic amines replaces the X attached to the CH$_2$ of the A-CH$_2$—X. Thus X is preferably a leaving group suitable for a nucleophilic reaction.

As used herein, and is well known in the art, the phrase "leaving group" describes a labile atom, group or chemical moiety that readily undergoes detachment from an organic molecule during a chemical reaction, while the detachment is facilitated by the relative stability of the leaving atom, group or moiety thereupon. Typically, any group that is the conjugate base of a strong acid can act as a leaving group. Representative examples of suitable leaving groups according to the present embodiments therefore include, without limitation, halide, acetate, tosylate, triflate, mesylate, sulfonate, azide, hydroxy, thiohydroxy, alkoxy, cyanate, thiocyanate, nitro and cyano. Preferably, the leaving group is selected from halide, acetate, tosylate, triflate, mesylate and sulfonate.

The term "acetate" refers to acetic acid anion.
The term "tosylate" refers to toluene-4-sulfonic acid anion.
The term "triflate" refers to trifluoro-methanesulfonic acid anion.
The term "azide" refers to an N$_3^-$.
The terms "cyanate" and "thiocyanate" refer to [O=C=N]$^-$ and [S=C=N]$^-$ anions respectively.

The process described hereinabove is preferably effected in the presence of a base, and more preferably, in the presence of an excess of a base, so as to prevent the formation of a corresponding salt. Any of the commonly used bases can be utilized, including, for example, carbonates, amines, and the like.

Alternatively, the process described hereinabove can further be effected by reacting the obtained product with an acid, so as to form the corresponding acid addition salt.

For further details regarding the reagents and conditions at which the process is preferably effected are delineated in the Examples section that follows.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

The compounds presented herein are all based on a heterotricyclic core (A in Formula I hereinabove), which is linked to a second moiety via a methylene group. The second moiety is any of 3 cyclic amines (B in Formula I hereinabove), which is linked to a heteroaryl moiety or an aryl moiety such as phenyl, pyridin-2-yl and pyrimidin-2-yl, each being substituted or unsubstituted (D in Formula I). As demonstrated hereinbelow (see, for example, Table 1), compounds having a variety of heterotricyclic cores have been prepared and practiced.

Based on their heterocyclic core, the compounds presented herein may be grouped into two families, as follows:

Family 1 comprises compounds having a 3H-pyrimido[4,5-b]benzo[d]thiophen-4-one heterotricyclic core moiety, or a derivative thereof in which the benzene ring of the heterotricyclic moiety is partially hydrogenated and/or substituted, which is linked to a second moiety, via position 2 of the 3H-pyrimido[4,5-b]benzo[d]thiophen-4-one (or the derivative thereof). Such compounds correspond to compounds having general Formula I above, in which A has Formula II (see general Formula I and Formula II hereinabove).

Family 2 comprises compounds having a 9H-pyrido[3,4-b]indole heterotricyclic core moiety, being substituted or non-substituted at the benzene ring, the indole nitrogen and/or the carbon at position 1 of the 9H-pyrido[3,4-b]indole, which is linked to a second moiety, via position 3 of the 9H-pyrido[3,4-b]indole. Such compounds correspond to compounds having general Formula I hereinabove, in which A has Formula III (see general Formula I and Formula III hereinabove).

The chemical structures of exemplary compounds of Families 1 and 2 which have been successfully prepared, are presented in Table 1 below.

Materials and Experimental Methods

Materials and Instrumental Data:
All reagents were commercially available and were used without further purification, unless otherwise indicated. Dry THF and diethyl ether were obtained by distillation from benzophenone sodium system under nitrogen immediately before use.

Column chromatography was carried out using silica gel 60 (230-400 mesh).

J.T. Baker flexible thin layer chromatography sheets (silica gel IB2-F) were used to monitor reactions.

$^1$H-NMR spectra were recorded using a 300 MHz Bruker ARX-300NMR spectrometer. Chemical shifts are reported in δ values ppm relative to an internal reference (0.03%, v/v) of tetramethylsilane (TMS) in $CDCl_3$, unless otherwise indicated.

Activity Assays:

Binding to Dopamine Receptor:

Compounds were assayed for competitive binding to the $D_{4.4}$ type dopamine receptors, which is expressed as human recombinant proteins in CHO cells, as described, for example, in Jarvis et al. (1973); Van Tol et al. (1991) and Van Tol et al. (1992).

Determination of binding to D4.4 receptor was performed using [$^3$H]-YM-09151-2 (70-87 Ci/mmol, 0.3 nM), as a radioligand, in with the presence of various concentrations of the tested compound. Reactions were carried out in 50 mM TRIS-HCl (pH 7.4) containing 5 mM $MgCl_2$, 5 mM EDTA, 5 mM KCl and 1.5 mM $CaCl_2$, for 60 minutes at 22° C. The reaction was terminated by rapid vacuum filtration onto glass fiber filters. Radioactivity trapped onto the filters was determined (counted) and compared to control values in order to accurately evaluate any interaction of the tested compound(s) with the cloned dopamine D4.4 binding site.

Binding to 5-$HT_{1A}$ Receptor:

Compounds were assayed for competitive binding to the 5-$HT_{1A}$ type serotonin receptor. The receptor is expressed as human recombinant proteins in HEK-293 cells, as described, for example, in Hoyer et al. (1985) and Schoeffter and Hoyer (1989).

Determination of binding to 5-$HT_{1A}$ receptor was performed using [$^3$H]-8-OH-DPAT, a 5-$HT_{1A}$ receptor ligand (Hoyer et al., 1985), as a radioligand (221 Ci/mmol, 0.5 nM) in the presence of various concentrations of the tested compound. Reactions were carried out in 50 mM Tris-HCl (pH 7.4) containing 10 mM $MgSO_4$, 0.5 mM EDTA, and 0.1% ascorbic acid for 60 minutes at 25° C. The reaction was terminated by rapid vacuum filtration onto glass fiber filters. Radioactivity trapped onto the filters was determined (counted) and compared to control values in order to accurately evaluate any interaction of the test compound(s) with the cloned 5-$HT_{1A}$ receptor binding site.

GTPγS Cellular 5-$HT_{1A}$ Activity:

Human recombinant serotonin 5-$HT_{1A}$ receptors expressed in CHO cells were used. The tested compound were incubated with cell membranes and [$^{35}$S]GTPγS for 30 minutes in modified HEPES buffer (pH=7.4). Test compound-induced increase of [$^{35}$S]GTPγS binding was quantified relative to serotonin-induced increase of [$^{35}$S]GTPγS. Compounds were tested at concentrations of 10, 1 and 0.1 µM.

In Vivo Activity Assay:

Penile erection was tested in Sprague Dawley rats. The experimental group included 50 adult male rats, with body weights in the range of 312-330 grams. The animals were housed for acclimatization in a cage, and water and food were supplied ad libitum.

Penile erection experiments were carried out in morning hours between 9 AM and 11 AM, in a dark room with a red light source. Control groups included 10 animals that received saline as a placebo, and 10 animals that received 0.3 µmol/kg body weight of apomorphine hydrochloride in 1 ml of saline, as a positive control.

The test group included 30 animals that were treated with a dose of 0.3 µmol/kg in 1 ml of saline of the tested compound, injected subcutaneously.

Ferret Emesis Model:

Male ferrets (*Mustela putorius furo*) were made to fast overnight before experiments. 18 animals (weighing 0.8-1.0 kg) were divided into the following three groups of six:

(1) test group—received the compound being tested, e dissolved in 1 ml saline at a dose of 0.3 µmol/kg body weight, administered subcutaneously;

(2) negative control—received saline; and (3) positive control—received apomorphine.

Animals were placed individually in observation cages and received cat food 30 minutes before the experiment.

One ml of saline was administered subcutaneously. Apomorphine and the test compound were dissolved in 1 ml saline at a dose of 0.3 µmol/kg body weight. Induced emesis or nausea was determined by direct observation during 90 minutes following drug injection. Nausea was characterized by behavior such as licking, gagging, backing, head burying and intense abdominal grooming. Emesis was characterized by rhythmic abdominal contractions.

Example 1

Preparation of Family 1 Compounds—General Procedure

The general synthetic pathway for preparing Family 1 compounds is depicted in Schemes 3(a) and 3(b) below:

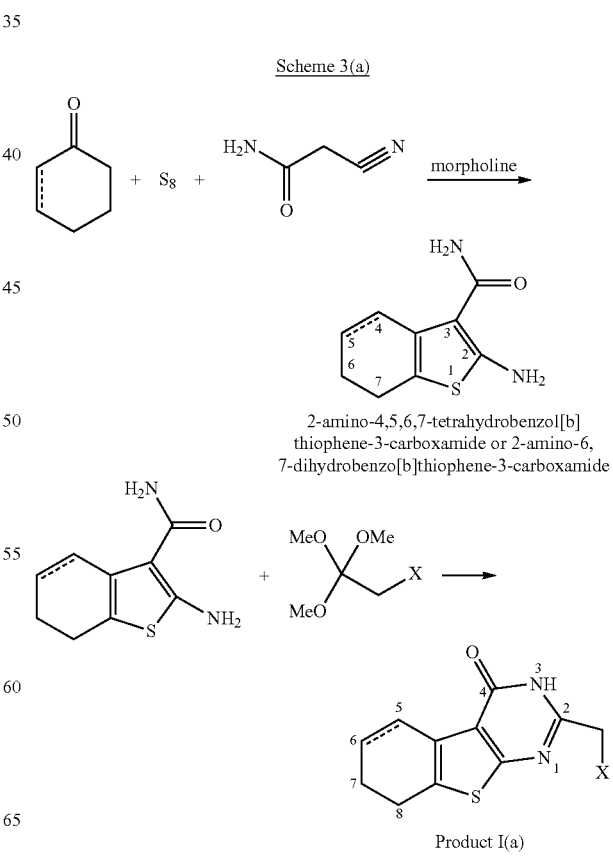

Product I(a)

-continued

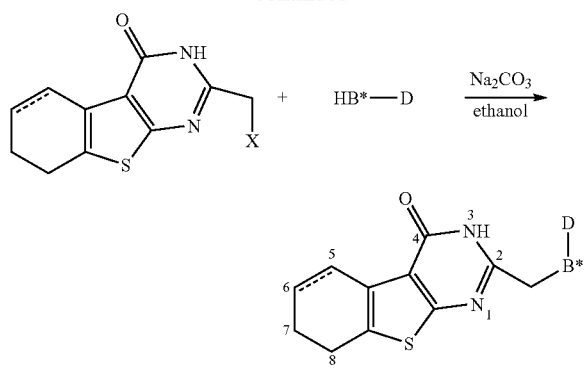

Scheme 3(b)

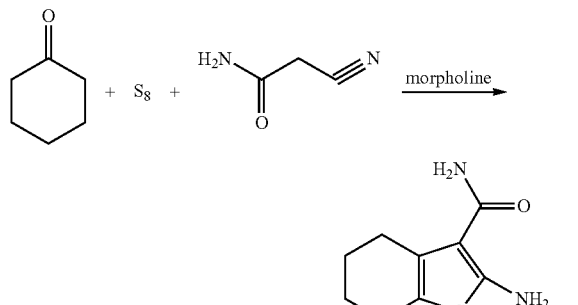

2-amino-4,5,6,7-tetrahydrobenzo[b]thiophene-3-carboxamide

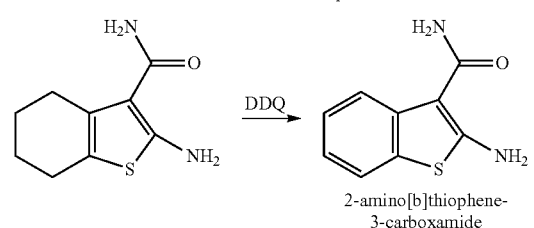

2-amino[b]thiophene-3-carboxamide

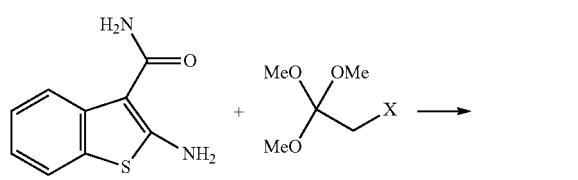

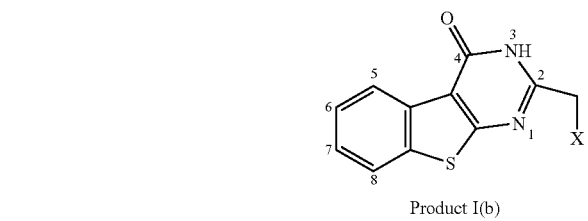

Product I(b)

-continued

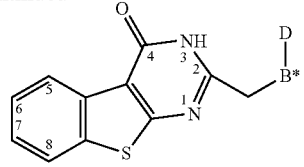

wherein:
X is a suitable leaving group such as, for example, halide, mesylate and triflate, and is preferably halide (e.g., chloride);
the dashed line denoted a saturated bond or an unsaturated (double) bond;
Product I(a) is 5,6,7,8-tetrahydro-3H-pyrimido[4,5-b]benzo[d]thiophen-4-one or 7,8-dihydro-3H-pyrimido[4,5-b]benzo[d]thiophen-4-one (or a derivative thereof), attached at position 2 thereof to a methylene group bound to X.
Product I(b) is 9H-pyrido[3,4-b]indole (or a derivative thereof) attached at position 3 thereof to a methylene group bound to X.
HB*-D is a cyclic amine, containing a nucleophilic nitrogen atom, selected from the following groups:

(a)
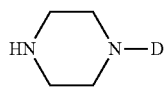

(b)
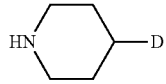

(c)
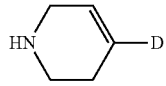

such that B* is B as defined hereinabove for general Formula I absent a CH$_2$ group bound to a nitrogen atom thereof; and D is selected from the group consisting of:

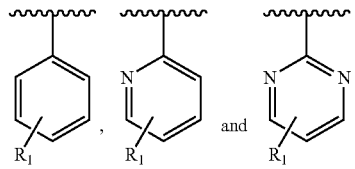

whereas R$_1$ is selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted, as defined hereinabove.

Cyclohexanone (or substituted cyclohexanone) is added dropwise to a mixture of sulfur and cyanoacetamide in a polar solvent such as ethanol, wherein the cyclohexanone, cyanoacetamide and sulfur atoms are at approximately equimolar amounts. An approximately equimolar amount of morpholine is then slowly added, and the mixture is stirred overnight at approximately 50-60° C., and then cooled to room temperature. 2-amino-4,5,6,7-tetrahydrobenzo[b]

thiophene-3-carboxamide (or a derivative thereof) is filtered, washed with a polar solvent such as methanol and dried by vacuum.

The 2-amino-4,5,6,7-tetrahydrobenzo[b]thiophene-3-carboxamide (or derivative thereof) is suspended in a non-polar solvent such as toluene and heated to reflux. A slight molar excess (e.g. a 3:2 molar ratio) of 1,1,1-trimethoxyethane substituted with a suitable leaving group at the 2 position is then added, and the mixture is then heated. A precipitate is formed, which is then filtered and dried by vacuum, giving Product I(a).

Product I(a) is mixed with an approximately equimolar amount of the nucleophile HB-D in an alcoholic solvent such as ethanol with a molar excess of a base such as sodium carbonate, while refluxing the reaction mixture for a few hours. The solvent is thereafter evaporated and the crude product is optionally purified by column chromatography (e.g., on a silica gel with elution by a 9:1 mixture of ethylacetate and methanol) to yield the final product with a 5,6,7,8-tetrahydro-3H-pyrimido[4,5-b]benzo[d]thiophen-4-one heterotricyclic core moiety.

To obtain a final product with a 7,8-dihydro-3H-pyrimido[4,5-b]benzo[d]thiophen-4-one heterotricyclic core moiety, 2-cyclohexenone (or substituted 2-cyclohexenone) is used as a precursor instead of cyclohexanone.

To obtain a final product with a 3H-pyrimido[4,5-b]benzo[d]thiophen-4-one heterotricyclic core moiety, the 2-amino-4,5,6,7-tetrahydrobenzo[b]thiophene-3-carboxamide (or derivative thereof) intermediate is mixed with an oxidizing agent such as of 2,3-dicyano-5,6-dichloro-parabenzoquinone (DDQ) in a non-polar solvent such as toluene at room temperature. The reaction is mixed for a few hours at moderate heat (e.g. 40° C.). The solvent is then removed under reduced pressure, and the residue is filtered and then optionally purified by column chromatography (e.g., on a silica gel with elution by a 8:2 mixture of dichloromethane and ethylacetate) to yield 2-aminobenzo[b]thiophene-3-carboxamide (or derivative thereof). This intermediate is then reacted according to the general procedure described above, in place of the 2-amino-4,5,6,7-tetrahydrobenzo[b]thiophene-3-carboxamide intermediate (see Scheme 3(b)).

Using this general procedure, Compounds B-92, B-93, B-94, B-95 and C1 to C20 (see Table 1) have been prepared.

In a typical example, the Compound C10 (see, Table 1) was prepared as follows:

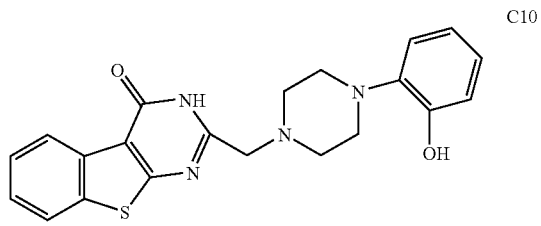

C10

33 ml of cyclohexanone was added dropwise to a mixture of 11 grams sulfur and 29 grams cyanoacetamide in 70 ml of ethanol. 30 ml of morpholine was then slowly added, and the mixture was stirred at 50-60° C. for 20 hours and then cooled to the room temperature. The intermediate, 2-amino-4,5,6,7-tetrahydrobenzo[b]thiophene-3-carboxamide, was filtered, washed with cool methanol and dried by vacuum. The yield was 52 g.

1.96 grams (10 mmol) of 2-amino-4,5,6,7-tetrahydrobenzo[b]thiophene-3-carboxamide was slowly treated with 9.0 grams (40 mmol) DDQ in toluene at room temperature. The reaction was mixed at 40° C. for 15 hours, and monitored by GLC. The solvent was then removed under reduced pressure, and the residue was transferred to 10 ml of dichloromethane and filtered via Celite. The filtrate was purified by chromatography on silica gel, using dichloromethane and ethyl acetate (at an 8:2 ratio), yielding 1.4 grams (70% yield) of 2-aminobenzo[b]thiophene-3-carboxamide as yellow powder.

1.4 grams (5.6 mmol) of 2-aminobenzo[b]thiophene-3-carboxamide was dissolved in 100 ml of toluene, and the solution was heated to reflux. 1.5 grams (10 mmol) of 2-chloro-1,1,1-trimethoxyethane was added, and the mixture was then heated for 45 minutes, while 10 mg of para-toluene sulfonic acid was added. Within a few minutes, a white powder separated. The powder was filtered and dried by vacuum, giving 1.0 grams (72% yield) of Product I(b).

250 mg (1 mmol) of Product I(b) and 178 mg (1 mmol) of 1-(2-hydroxyphenyl)piperazine were mixed in ethanol with 318 mg of sodium carbonate. The mixture was then refluxed for 10 hours. Thereafter, the ethanol was distilled off under reduced pressure, and the resulting residue was transferred to a 2:1 mixture of dichloromethane and water. The organic phase was separated, the solvent evaporated, and the final product was then purified by column chromatography using a 9:1 mixture of ethylacetate and methanol. 338 mg of C10 was obtained (78% yield).

$^1$H-NMR (CDCl$_3$): δ=12.1 (bs, 1H, NH), 8.20-6.50 (m, 8H, H$_{ar}$), 3.87 (s, 2H), 3.35-3.24 (t, 4H), 2.84-2.55 (t, 4H) ppm.

Example 2

Preparation of Family 2 Compounds—General Procedure

The general synthetic pathway for preparing Family 2 compounds is depicted in Scheme 4 below:

Scheme 4

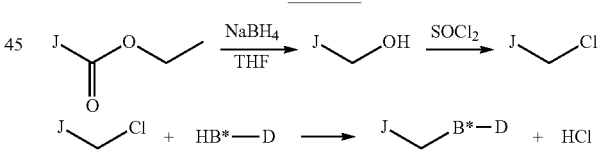

wherein:

J is 9H-pyrido[3,4-b]indole (β-carboline) or a substituted derivative thereof;

HB*-D is a cyclic amine selected from the following groups:

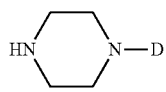

(a)

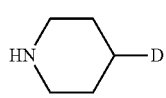

(b)

-continued

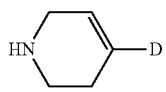
(c)

such that B* is B as defined hereinabove for general Formula I absent a $CH_2$ group bound to a nitrogen atom thereof; and D is selected from the group consisting of:

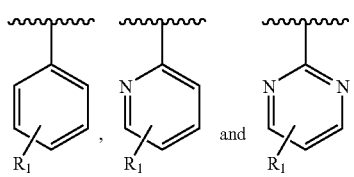

whereas $R_1$ is selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted, as defined hereinabove.

3-carboethoxy-β-carboline or a derivative thereof (J in Scheme 4 above) is dissolved in a polar solvent (e.g., THF), and a reducing agent (e.g., $NaBH_4$) is added to the solution. The mixture is stirred for a few hours and cooled. An excess of water is then added, and the mixture is stirred for another few hours. The solvent is thereafter evaporated and the resulting residue is dissolved in water, washed several times with one or more non-polar solvents such as dichloromethane and ethyl acetate, and the combined organic extracts are then evaporated. The remaining residue is purified by column chromatography (e.g., on a silica gel with elution by a 9:1 mixture of ethylacetate and methanol), to give a 3-hydroxymethyl-β-carboline intermediate.

The intermediate is added to an excess of thionyl chloride, and the mixture is refluxed for approximately 1 hour. The excess thionyl chloride is then evaporated and a residue of a 3-(chloromethyl)-β-carboline intermediate is crystallized from hexane.

Alternatively, the hydroxymethyl carboline can be reacted with other reagents, such as triflic anhydride or mesyl chloride, so as to produce a carboline substituted by a moiety that contains a leaving group other than chloride.

The obtained residue is then reacted with an approximately equimolar amount of a cyclic nucleophile (HB*-D in Scheme 4 above), in the presence of an excess of a base such as $Na_2CO_3$ in an alcoholic solvent (e.g., ethanol), while refluxing the reaction mixture for a few hours. The solvent is thereafter evaporated and the crude product is optionally purified by column chromatography to yield the final product.

Since excess of base is used, the salt HCl (or any other salt, depending on the leaving group), is obtained as a by-product, whereby the product itself is obtained in a free base form.

Optionally, the product is converted to its corresponding salt by dissolving the product in an organic solvent (e.g., chloroform) and adding to this solution an organic (e.g., ethereal) solution of the respective acid (e.g., HCl). The salt separates immediately from the mixture as a precipitate.

Using this general procedure, Compounds B-96, B-97, B-98 and B-99 (see Table 1) have been prepared.

In a typical example, 3-(4-((9H-pyrido[3,4-b]indol-3-yl)methyl)piperazin-1-yl)phenol (Compound B-98) was prepared as follows:

3.5 grams (15 mmol) of 3-carboethoxy-β-carboline were suspended in 300 ml THF, 2.7 grams (75 mmol) sodium borohydride were added and the mixture was stirred at room temperature for 12 hours. The mixture was then cooled, 50 ml water were added and the resulting mixture was stirred overnight. The solvent was evaporated under reduced pressure and water (300 ml) was again added. The aqueous suspension was extracted with dichloromethane, followed by ethylacetate, the organic extracts were combined, and the solvent was evaporated under reduced pressure. The remaining residue was purified by column chromatography on silica gel, using and a 9:1 mixture of ethylacetate and methanol as eluent, to give 3-(hydroxymethyl)-β-carboline (2.5 grams, 81% yield).

The 3-(hydroxymethyl)-β-carboline was added to an excess (3 grams) of thionyl chloride and the mixture was refluxed for 1 hour. The excess thionyl chloride was then evaporated and the obtained residue was crystallized from hexane. 2.5 grams of 3-(chloromethyl)-β-carboline was obtained.

216 mg (1 mmol) of 3-(chloromethyl)-β-carboline and 178 mg (1 mmol) of 1-(3-hydroxyphenyl)piperazine were mixed in ethanol, 318 mg of sodium carbonate were added and the mixture was refluxed for 7 hours. Thereafter, the ethanol was distilled under reduced pressure, and the remaining residue was collected in a 2:1 mixture of dichloromethane and water. The organic phase was separated, the solvent was evaporated and the product was then purified by column chromatography using a 9:1 mixture of ethyl acetate and methanol as eluent, to give 214 mg (60% yield) of the final product.

$^1$H-NMR ($CDCl_3$): δ=11.70 (bs, 1H, NH), 8.61-6.11 (m, 10H, $H_{ar}$), 3.70 (s, 2H), 3.34-3.23 (t, 2H), 2.83-2.52 (t, 4H) ppm.

Example 3

In Vitro Activity Assays

The results obtained in the assays for D4.4 and 5-$HT_{1A}$ binding described hereinabove, for some of the exemplary compounds described herein, are presented in Table 2 below. An observed activity that was not quantified is designated as "active".

As can be seen in Table 2, substantial selective binding of D4.4 dopamine receptor was observed with many compounds at micromolar and even submicromolar concentrations.

Additionally, a selective binding to 5-$HT_{1A}$ receptor was also observed in many compounds at micromolar concentrations.

Importantly, as can further be seen in Table 2, several compounds were found to exhibit selective binding to both D4.4 and 5-$HT_{1A}$ receptors, indicating dual serotonergic and dopaminergic activity.

As further presented in Table 2, Compounds B-94 and B-97 were tested by a [$^{35}$S]GTPγS assay, and found to activate 5-$HT_{1A}$ receptor, at concentrations of 10 μM, to 50% and 48% respectively of the degree of activation by serotonin. These results indicate that the binding of 5-$HT_{1A}$ receptor by these compounds activates the receptor.

Example 4

In Vivo Activity Assays

Rats Model:

Penile erection was tested in Sprague Dawley rats, according to the protocol described hereinabove. The obtained results are presented in FIG. 1.

As shown in FIG. 1, 26 of the 30 animals (87%) treated with 0.3 mmol/kg B-99 showed moderate to strong erection, during 45-70 minutes.

The positive control group (treated 0.3 mmol/kg apomorphine) showed a 70% response during 15-25 minutes. No erection was observed in the negative control group.

Ferret Emesis Model:

B-99 was administered to ferrets in order to evaluate the appearance of adverse side effects of emesis and nausea. The results are presented in FIG. 2.

Figure 2:
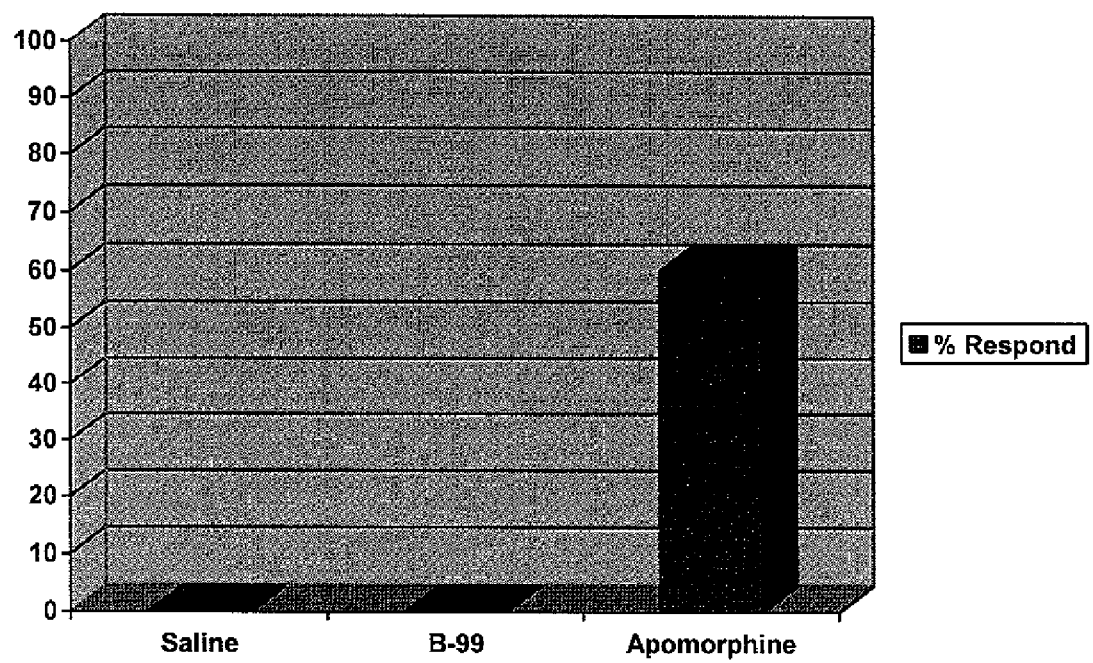
FIG. 2 is a bar graph presenting the results obtained in in vivo studies in ferrets, and demonstrating the absence of appearance of the adverse side effects emesis and nausea, following treatment with B-99, an exemplary compound according to the present embodiment, as compared to apomorphine.

As shown in FIG. 2, none of the 6 ferrets receiving saline and none of the 6 ferrets receiving 0.3 µmol/kg B-99 exhibited signs of nausea or emesis, such as licking, gagging, backing up, head burying, intense abdominal grooming, and rhythmic abdominal contractions. In comparison, 4 of the 6 ferrets receiving 0.3 µmol/kg apomorphine showed signs of nausea and/or emesis.

These results indicate that B-99 offers a significant advantage over apomorphine, as it facilitates penile erection without inducing nausea or emesis.

TABLE 1

| Compound | Structure |
|---|---|
| B-92 | (structure) |
| B-93 | (structure) |
| B-94 | (structure) |
| B-95 | (structure) |
| B-96 | (structure) |
| B-97 | (structure) |
| B-98 | (structure) |
| B-99 | (structure) |
| C1 | (structure) |
| C2 | (structure) |

TABLE 1-continued

| Compound | Structure |
|---|---|
| C3 | 2-methoxyphenyl piperazinyl methyl tetrahydrobenzothieno pyrimidinone |
| C4 | 2-ethoxyphenyl piperazinyl methyl tetrahydrobenzothieno pyrimidinone |
| C5 | 2-propoxyphenyl piperazinyl methyl tetrahydrobenzothieno pyrimidinone |
| C6 | phenyl piperazinyl methyl tetrahydrobenzothieno pyrimidinone |
| C7 | 4-phenylpiperidinyl methyl tetrahydrobenzothieno pyrimidinone |
| C8 | 4-phenyl-1,2,3,6-tetrahydropyridinyl methyl tetrahydrobenzothieno pyrimidinone |
| C9 | 2-(pyridin-2-yl)piperazinyl methyl benzothieno pyrimidinone |
| C10 | 2-hydroxyphenyl piperazinyl methyl benzothieno pyrimidinone |
| C11 | 3-hydroxyphenyl piperazinyl methyl benzothieno pyrimidinone |
| C12 | 2-(pyrimidin-2-yl)piperazinyl methyl benzothieno pyrimidinone |
| C13 | 2-chlorophenyl piperazinyl methyl benzothieno pyrimidinone |
| C14 | 2-methoxyphenyl piperazinyl methyl benzothieno pyrimidinone |

TABLE 1-continued

| Compound | Structure |
|---|---|
| C15 | 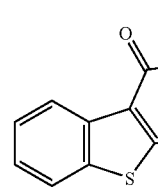 |
| C16 | 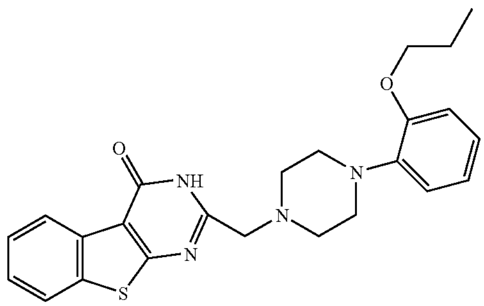 |
| C17 | 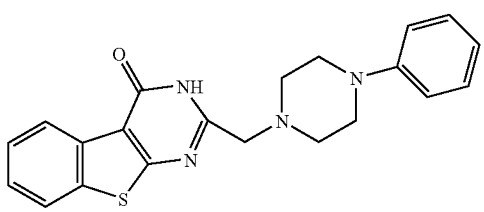 |
| C18 | 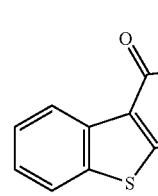 |
| C19 | |
| C20 | |

TABLE 2

| Compound No. | D4.4(h) receptor | | 5HT1A receptor | | | | | % activation of 5HT1A at 10 μM |
|---|---|---|---|---|---|---|---|---|
| | Competitive Binding, % at 100 nM | Competitive Binding, % at 1 μM | Binding % at 1 nM | Binding % at 10 nM | Binding % at 100 nM | Binding % at 1 μM | Binding % at 5 μM | |
| B-96 | 87.6 | 102.45 | active | active | active | active | active | active |
| B-98 | 93.03 | 96.61 | active | active | active | active | active | active |
| B-94 | 19.14 | 89.02 | 0.9 | 20.23 | 44.56 | 62.77 | 97.67 | 50 |
| B-95 | 32.26 | 86.68 | active | active | active | active | active | active |
| B-93 | 16.69 | 81.97 | active | active | active | active | active | active |
| B-97 | 74.27 | 100.99 | 1.78 | 37.48 | 75.08 | 99.45 | 100.34 | 48 |
| B-99 | 97.43 | 102.4 | active | active | active | active | active | active |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

LIST OF REFERENCES CITED

Alcantara, A. G. 1999, *J. Sex Marital Ther.*, 25:125-129
Andersson, K. *Pharmacol. Rev.* 2001, 53, 417-450.
Andrews, R, Cowley, A. J. *Drug Safety* 1993, 404
Ashton, A. K. *Am J Psychiatry.* 2004, 161:2133
Balon, R. 1996, *J. Sex Marital Ther.*, 22:290-292
Beavo, J. A. *Physiol. Rev.* 1998, 75, 725.
Ben Zion, I. Z., Tessler, R., Cohen, L., Lerer, E., Raz, Y, Bachner-Melman, R., Gritsenko, I., Nemanov, L., Zohar, A. H., Belmaker, R. H., Benjamin, J., Ebstein, R. P. 2006, *Mol. Psychiatry*, 11:782-786
Brioni, J. D., Moreland, R. B., Cowart, M., Hsieh, G. C., Stewart, A. O., Hedlund, P., Donnelly-Roberts, D. L., Nakane, M., Lynch, J. J., III, Kolasa, T., Polakowski, J. S., Osinski, M. A., Marsh, K., Andersson, K. E., Sullivan, J. P. *Proc. Natl. Acad. Sci. U.S.A.* 2004, 101, 6758.
Burnett, A. L. *Nitric oxide in the penis; physiology and pathology. Journal of Urology* 1997, 157, 320-324.
Corbin, J. D., Francis, S. H. *Cyclic GMP phosphodiesterase-5: target of sildenafil. Journal of Biological Chemistry* 1999, 274, 13729-13732.
Corbin, J. D., Francis, S. H., Webb, D. J. *Phosphodiesterase type 5 as a pharmacologic target in erectile dysfunction.* Urology 2002, 60, 4-11.
Cowart, M., Latshaw, S. P., Bhatia, P., Daanen, J. F., Rohde, J., Nelson, S. L., Patel, M., Kolasa, T., Nakane, M, Uchic, M. E., Miller, L. N., Terranova, M. A., Chang, R., Donnely-Roberts, D. L., Namovic, M. T., Hollingsworth, P. R., Martino, B., Lynch, J. J., Sullivan, J., Hsieh, G. C., Moreland, R. B., Brioni, J. D., Stewart, A. O. *J. Med. Chem.* 2004, 47(15), 3853-64.
Damis, M, Patel, Y, Simpson, G. M. *Prim. Care Companion J. Clin. Psychiatry* 1999, 1:184-187
Dumaitre, B., Dodic, N. *J. Med. Chem.* 1996, 39, 1635.
Evans L. E., Bett, J. H., Cox, J. R., Dupois, J. P., Van Hees, T. *Prog. Neuropsychopharmacol.* 1980, 4:293-302
Francis, S. H., Corbin, J. D. *Methods Enzym.* 1988, 159, 722.
Hoyer, D., Engel G. *Eur. J. Pharmacol.* 1985, 118:13-23
Hyttel, J. *Prog. Neuro-Psychopharmacol. Biol. Psychiat.* 1982, 6:277-95
Giuliano, F., Allard, J. 2001, *Int. J. Impot. Res.*, 13 Suppl. 3:S18-28
Gundlach, A. L., Largent, B. L., Snyder, S. H. *Life Sciences* 1984, 35:1981-1988
Jarvis, K. R., Tiberi, M, Silvia, C., Gingrich, J. A. and Caron, M. G. *J. Receptor Research* 1973, 13(1-4): 573-590
Melis, M. & Argiolas, A. *Neurosci. Biobehav. Rev.* 1995, 19, 19-38.
Melis, M. R., Succu, S., Sanna, F., Melis, T., Mascia, M. S., Enghard-Gueiffier, C., Hubner, H., Gmeiner, P., Gueiffier, A., Argiolas, A. *Eur. J. Neurosci.* 2006, 24:2021-2030
Missale, C., Nash, S., Robinson, S., Jaber, M. & Caron, M. *Physiol. Rev.* 1998, 78, 189-225
Missale, C., Nash, S., Robinson, S., Jaber, M. & Caron, M. *Physiol. Rev.* 1998, 78, 189-225
Modell, J. G., May, R. S., Katholi, C. R. *J. Sex Marital Ther.* 2000, 26:231-240
Moreland, R. B., Goldstein, I., Traish, A. *Life Sci.* 1995, 62, PL309.
Moreland, R. B., Hsieh, G., Nakane, M, Brioni, J. D. *J. Pharm. Exper. Therap.* 2001, 296, 225.
Moreland, R. B., Patel, M, Hsieh, G. C., Wetter, J. M, Marsh, K., Brioni, J. D. *Pharmacol. Biochem. Behav.* 2005, 82:140-147
Nakane, M, Cowart, M. D., Hsieh, G. C., Miller, L., Uchic, M. E., Chang, R., Terranova, M. A., Donnely-Roberts, D. L., Namovic, M. T., Miller, T. R., Wetter, J. M., Marsh, K., Stewart, A.)., Brioni, J. D., Moreland, R. B. *Neuropharmacology* 2005, 49:112-121
Rotella D P. *Phosphodiesterase 5 inhibitors: current status and potential applications.* Nat Rev Drug Discov. 2002 September; 1(9):674-82.
Schoeffter, P., Hoyer, D., *Naunyn-Schmiedeberg's Arch. Pharmac.* 1989, 340:135-138
Stimmel, G. L., Gutierrez, M. A. 2006, *CNS Spectr.*, 11:24-30
Takase, Y, Saeki, T., Watanabe, N., Adachi, H., Souda, S., Saito, I. *J. Med. Chem.* 1993, 37, 2104.
Takase, Y., Saeki, T., Fujimoto, M, Saito, I. *J. Med. Chem.* 1994, 36,3765.
Terret, N. K., Bell, A. S., Brown, D., Ellis, P. *Bioorg. Med. Chem. Lett.* 1996, 6, 1819.
Ukida, T., Nakamura, Y., Kubo, A., Yamamoto, Y., Takahashi, M., Kotera, J., Ikeo, T. *J. Med. Chem.* 1999, 42, 1293
Ukida, T., Nakamura, Y., Kubo, A., Yamamoto, Y., Moritani, Y., Saruta, K., Higashijima, T., Kotera, J., Takagi, M., Kikkawa, K., Omori, K. *J. Med. Chem.* 2001, 44, 2204.
Van Tol H. H., Bunzow, J. R., Guan, H. C., Sunahara, R. K., Seeman, P., Niznik, H. B., Civelli, O. *Nature* 1991, 350: 610-614
Van Tol H. H., Wu, C. M, Guan, H. C., Ohara, K., Bunzow, J. R., Civelli, O., Kennedy, J., Seeman, P., Niznik, H. B., Jovanovic, V. *Nature* 1992, 358: 149-152
Watanabe, N., Adachi, H., Takase, Y, Ozaki, H., Matsukura, M., Miyazaki, K., Kabasawa, Y. *J. Med. Chem.* 2000, 43, 2523.
Wolters, J. P., Hellstrom, W. *J. Rev. Urol.* 2006, 8, Suppl. 4:S18-25

What is claimed is:
1. A compound having the Formula I:

$$A\text{-}B\text{-}D \qquad \text{Formula I}$$

or a pharmaceutically acceptable salt thereof,
wherein:
A is selected from the group consisting of a moiety having Formula II and a moiety having general Formula III:

Formula II

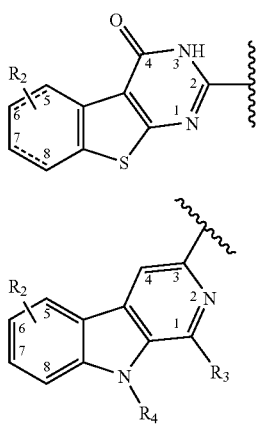

Formula III

B is a moiety selected from the group consisting of:

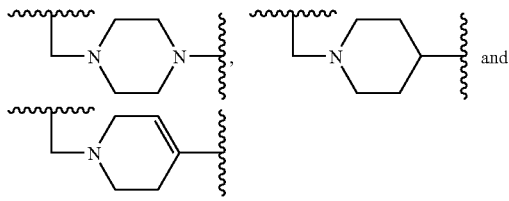

D is:

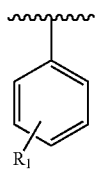

whereas:
a dashed line denotes a saturated or non-saturated bond; and
R₁-R₄ are each independently selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

2. The compound of claim 1, wherein R₂-R₄ are each hydrogen.

3. The compound of claim 1, wherein A is said moiety having general Formula II.

4. The compound of claim 3, wherein each of the dashed lines denotes a saturated bond.

5. The compound of claim 4, wherein B is

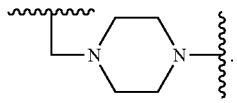

6. The compound of claim 5, wherein R₁ is selected from the group consisting of hydroxy and alkoxy.

7. The compound of claim 4, wherein B is

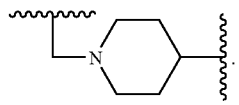

8. The compound of claim 3, wherein one of the dashed lines denotes a non-saturated bond and the other dashed line denotes a saturated bond.

9. The compound of claim 8, wherein B is

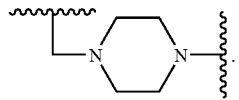

10. The compound of claim 9, wherein R₁ is selected from the group consisting of hydrogen, hydroxy and alkoxy.

11. The compound of claim 8, wherein B is

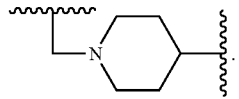

12. The compound of claim 8, wherein B is

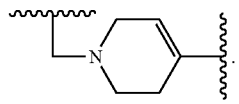

13. The compound of claim 3, wherein each of the dashed lines is an unsaturated bond.

14. The compound of claim 13, wherein B is

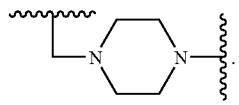

15. The compound of claim 14, wherein R₁ is selected from the group consisting of hydrogen, halo, hydroxy, and alkoxy.

16. The compound of claim 13, wherein B is

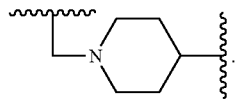

17. The compound of claim 13, wherein B is

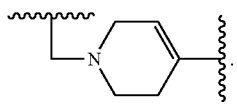

18. A compound having the Formula I:

A-B-D    Formula I or a pharmaceutically acceptable salt thereof,
wherein:
A is a moiety having Formula III:

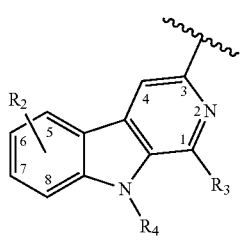

Formula III

B is a moiety selected from the group consisting of:

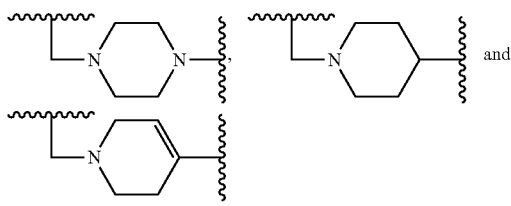

D is a moiety selected from the group consisting of:

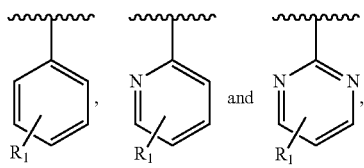

whereas:
$R_1$-$R_4$ are each independently selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

19. The compound of claim 18, wherein B is

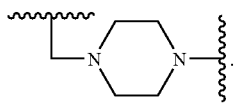

20. The compound of claim 19, wherein D is

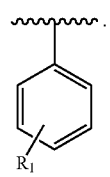

21. The compound of claim 20, wherein $R_1$ is selected from the group consisting of hydrogen, hydroxy, and alkoxy.

22. A pharmaceutical composition comprising, as an active ingredient, the compound of claim 1 and a pharmaceutically acceptable carrier.

23. The pharmaceutical composition of claim 22, being packaged in a packaging material and identified in print, in or on said packaging material, for use in the treatment of a sexual disorder.

24. A method of treating a sexual disorder, the method comprising administering to a subject in need thereof the compound of claim 1.

25. A process of preparing the compound of claim 1, the process comprising:
reacting a compound having the Formula:

A-CH$_2$—X wherein X is a leaving group,
and a compound selected from the group consisting of:

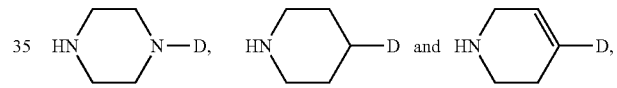

thereby obtaining the compound having said Formula I.

26. A compound having the Formula I:

A-B-D    Formula I or a pharmaceutically acceptable salt thereof,
wherein:
A is selected from the group consisting of a moiety having Formula II and a moiety having Formula III:

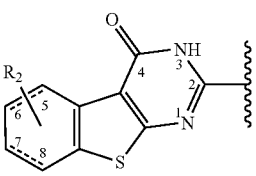

Formula II

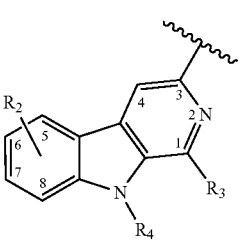

Formula III

B is

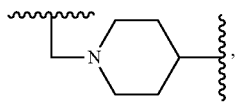

D is a moiety selected from the group consisting of:

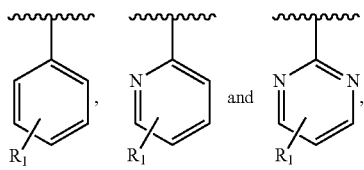

whereas:

a dashed line denotes a saturated or non-saturated bond; and

R$_1$-R$_4$ are each independently selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

27. The compound of claim 26, wherein R$_2$-R$_4$ are each hydrogen.

28. The compound of claim 26, wherein A is said moiety having general Formula II.

29. The compound of claim 28, wherein each of the dashed lines denotes a saturated bond.

30. The compound of claim 26, wherein D is

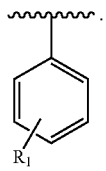

31. The compound of claim 30, wherein R$_1$ is selected from the group consisting of hydrogen, hydroxy and alkoxy.

32. The compound of claim 28, wherein one of the dashed lines denotes a non-saturated bond and the other dashed line denotes a saturated bond.

33. The compound of claim 28, wherein each of the dashed lines is an unsaturated bond.

34. A compound having the Formula I:

A-B-D    Formula I or a pharmaceutically acceptable salt thereof, wherein:

A is selected from the group consisting of a moiety having Formula II and a moiety having Formula III:

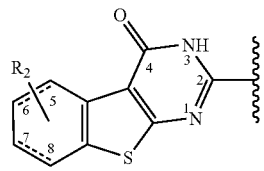
Formula II

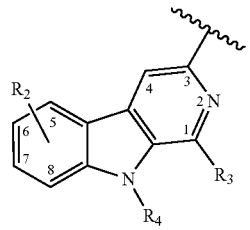
Formula III

B is a moiety selected from the group consisting of:

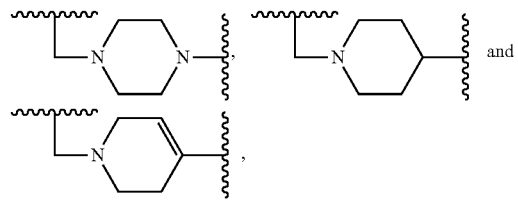

D is a moiety selected from the group consisting of:

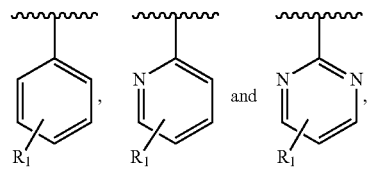

whereas:

a dashed line denotes a saturated or non-saturated bond, wherein 0 or 1 of the dashed lines denote a saturated bond; and R$_1$-R$_4$ are each independently selected from the group consisting of hydrogen, alkyl, hydroxy, alkoxy, thiohydroxy, thioalkoxy, halide, amine, amide, carbonyl, carboxy, thiocarboxy, ether, thioether, epoxide (oxirane), sulfonyl, sulfinyl, sulfonamide, nitro, nitrile, isonitrile, thiirane, aziridine, nitroso, hydrazine, carbamyl and thiocarbamyl, each being substituted or non-substituted.

35. The compound of claim 34, wherein R$_2$-R$_4$ are each hydrogen.

36. The compound of claim 34, wherein A is said moiety having general Formula II.

37. The compound of claim 36, wherein B is

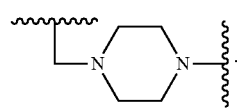

38. The compound of claim 37, wherein D is

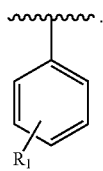.

39. The compound of claim 38, wherein $R_1$ is selected from the group consisting of hydrogen, hydroxy and alkoxy.

40. The compound of claim 36, wherein each of the dashed lines is an unsaturated bond.

41. The compound of claim 40, wherein B is

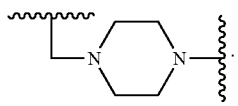

42. The compound of claim 41, wherein D is

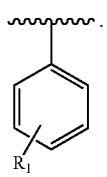.

43. A pharmaceutical composition comprising, as an active ingredient, the compound of claim 18 and a pharmaceutically acceptable carrier.

44. A kit comprising The pharmaceutical composition of claim 43, being packaged in a packaging material and identified in print, in or on said packaging material, for use in the treatment of a sexual disorder.

45. A method of treating a sexual disorder, the method comprising administering to a subject in need thereof the compound of claim 18.

46. A pharmaceutical composition comprising, as an active ingredient, the compound of claim 26 and a pharmaceutically acceptable carrier.

47. A method of treating a sexual disorder, the method comprising administering to a subject in need thereof the compound of claim 26.

48. A pharmaceutical composition comprising, as an active ingredient, the compound of claim 34 and a pharmaceutically acceptable carrier.

49. A method of treating a sexual disorder, the method comprising administering to a subject in need thereof the compound of claim 34.

50. The compound of claim 1, wherein:
A is said moiety having general Formula II;
each of the dashed lines denotes a saturated bond;
B is

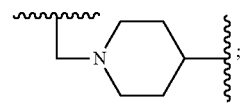

and
$R_1$ and $R_2$ are each hydrogen.

51. The compound of claim 1, wherein:
A is said moiety having general Formula II;
each of the dashed lines denotes a saturated bond;
B is

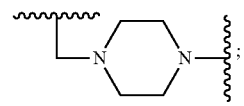

$R_1$ is selected from the group consisting of ethoxy and hydroxy; and
$R_2$ is hydrogen.

52. The compound of claim 1, wherein:
A is said moiety having general Formula III;
B is

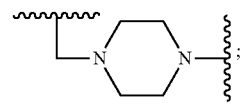

$R_1$ is selected from the group consisting of hydrogen, methoxy, ethoxy and hydroxy; and
$R_2$-$R_4$ are each hydrogen.

* * * * *